United States Patent
Karginov

(10) Patent No.: US 11,965,002 B2
(45) Date of Patent: Apr. 23, 2024

(54) OPTOGENETIC CONSTRUCT FOR ALLOSTERIC CONTROL OF PROTEIN ACTIVITY

(71) Applicant: THE BD OF TRUSTEES OF THE UNIVERSITY OF ILLINOIS, Urbana, IL (US)

(72) Inventor: Andrei Karginov, Chicago, IL (US)

(73) Assignee: THE BD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 10 days.

(21) Appl. No.: 16/699,203

(22) Filed: Nov. 29, 2019

(65) Prior Publication Data

US 2020/0172583 A1    Jun. 4, 2020

Related U.S. Application Data

(60) Provisional application No. 62/772,841, filed on Nov. 29, 2018.

(51) Int. Cl.
| | |
|---|---|
| A61K 47/65 | (2017.01) |
| A61K 41/00 | (2020.01) |
| A61K 41/17 | (2020.01) |
| C07K 14/37 | (2006.01) |
| C07K 14/415 | (2006.01) |
| C12N 9/12 | (2006.01) |
| C12N 15/90 | (2006.01) |
| C12N 15/85 | (2006.01) |

(52) U.S. Cl.
CPC .......... *C07K 14/37* (2013.01); *A61K 41/0042* (2013.01); *A61K 41/0057* (2013.01); *A61K 47/65* (2017.08); *C07K 14/415* (2013.01); *C12N 9/12* (2013.01); *C12N 15/90* (2013.01); *C07K 2319/00* (2013.01); *C12N 2015/859* (2013.01); *C12N 2800/30* (2013.01); *C12N 2800/80* (2013.01)

(58) Field of Classification Search
None
See application file for complete search history.

(56) References Cited

U.S. PATENT DOCUMENTS

| | | |
|---|---|---|
| 6,733,996 B2 | 5/2004 | Froehlich |
| 2014/0220615 A1 | 8/2014 | Zhou |
| 2016/0326219 A1 | 11/2016 | Riedler |
| 2020/0157514 A1* | 5/2020 | Sato ..................... C12N 9/1241 |

OTHER PUBLICATIONS

Pudasaini, A., et al. 2015 Frontiers in Molecular Bioscience 2(18): 15 pages. (Year: 2015).*
Chichili, V.P.R., et al. 2013 Protein Science 22: 153-167. (Year: 2013).*
Seifert, S., et al. 2018 ACS Chem Biol 13: 1914-1920. (Year: 2018).*
Leopold, A.V., et al. 2018 Chem Soc Rev 47: 2454-2484. (Year: 2018).*
Zoltowski, B.D., et al. 2008 Biochemistry 47(27): 7012-7019. (Year: 2008).*
Gurzov, E.N., et al. 2015 Trends in Endocrinology and Metabolism 26(1): 30-39. (Year: 2015).*
Chang, K.-Y., D. Woo, H. Jung, S. Lee, S. Kim, J. Won, T. Kyung, H. Park, N. Kim, H.W. Yang, J.-Y. Park, E.M. Hwang, D. Kim and W.D. Heo (2014) "Light-inducible receptor tyrosine kinases that regulate neurotrophin signaling," Nat. Commun. 5:4057.
Karginov, A.V., F. Ding, P. Kota, N.V. Dokholyan and K.M. Hahn (2010) "Engineered allosteric activation of kinases in living cells," Nat. Biotechnol. 28(7):743-747.
Karginov, A.V., D. Tsygankov, M. Berginski, P.-H. Chu, E.D. Trudeau, J.J. Yi, S. Gomez, T.C. Elston and K.M. Hahn (2014) "Dissecting signaling through activation of specific Src-effector complexes in vivo," Nat. Chem. Biol. 10(4):286-290.
Katsura, Y., H. Kuboto, K. Kunida, A. Kanno, S. Kuroda and T. Ozawa (2015) "An optogenetic system for interrogating the temporal dynamics of Akt," Sci. Rep. 5:14589.
Mills, E., X. Chen, E. Pham, S. Wong and K. Truong (2012) "Engineering a Photoactivated Caspase-7 for Rapid Induction of Apoptosis," ACS Synth. Biol. 1(3):75-82.
Wend, S., H.J. Wagner, K. Muller, M.D. Zurbriggen, W. Weber and G. Radziwill (2014) "Optogenetic control of protein kinase activity in mammalian cells," ACS Synth. Biol. 3(5):280-285.
Wu, Y.I., D. Frey, O.I. Lungu, A. Jaehrig, I. Schlichting, B. Kuhlman and K.M. Hahn (2009) "A genetically encoded photoactivatable Rac controls the motility of living cells," Nature 461(7260):104-108.
Zhou, X.X., H.K. Chung, A.J. Lam and M.Z. Lin (2012) "Optical control of protein activity by fluorescent protein domains," Science 338(6108):810-814.
Zhou, X.X., L.Z. Fan, P. Li, K. Shen and M.Z. Lin (2017) "Optical Control of Cell Signaling by Single-chain Photoswitchable Kinases," Science 355(6327):836-842.

* cited by examiner

*Primary Examiner* — Marsha Tsay
(74) *Attorney, Agent, or Firm* — Licata & Tyrrell P.C.

(57) ABSTRACT

A light-activated construct composed of two photoreceptive polypeptide domains connected to one another by a flexible linker is provided, as is a fusion protein containing the same and polynucleotides encoding said construct and fusion protein. Methods of making and using the light-activated construct and fusion protein are also provided.

30 Claims, 4 Drawing Sheets

Specification includes a Sequence Listing.

SEQUENCE LISTING

<160> NUMBER OF SEQ ID NOS: 55

<210> SEQ ID NO 1
<211> LENGTH: 186
<212> TYPE: PRT
<213> ORGANISM: Neurospora crassa

<400> SEQUENCE: 1

```
Met Ser His Thr Val Asn Ser Ser Thr Met Asn Pro Trp Glu Val Glu
1               5                   10                  15

Ala Tyr Gln Gln Tyr His Tyr Asp Pro Arg Thr Ala Pro Thr Ala Asn
                20                  25                  30

Pro Leu Phe Phe His Thr Leu Tyr Ala Pro Gly Gly Tyr Asp Ile Met
            35                  40                  45

Gly Tyr Leu Ile Gln Ile Met Asn Arg Pro Asn Pro Gln Val Glu Leu
    50                  55                  60

Gly Pro Val Asp Thr Ser Cys Ala Leu Ile Leu Cys Asp Leu Lys Gln
65                  70                  75                  80

Lys Asp Thr Pro Ile Val Tyr Ala Ser Glu Ala Phe Leu Tyr Met Thr
                85                  90                  95

Gly Tyr Ser Asn Ala Glu Val Leu Gly Arg Asn Cys Arg Phe Leu Gln
                100                 105                 110
```

```
Ser Pro Asp Gly Met Val Lys Pro Lys Ser Thr Arg Lys Tyr Val Asp
            115                 120                 125

Ser Asn Thr Ile Asn Thr Met Arg Lys Ala Ile Asp Arg Asn Ala Glu
        130                 135                 140

Val Gln Val Glu Val Asn Phe Lys Lys Asn Gly Gln Arg Phe Val
145                 150                 155                 160

Asn Phe Leu Thr Met Ile Pro Val Arg Asp Glu Thr Gly Tyr Arg
                165                 170                 175

Tyr Ser Met Gly Phe Gln Cys Glu Thr Glu
            180                 185

<210> SEQ ID NO 2
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 2

Gly Gly Gly Gly Ser
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Gly Gly Ser Gly
1

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 4

Ser Ala Gly Gly
1

<210> SEQ ID NO 5
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 5

Ser Ala Lys Thr Thr Pro Lys Leu Gly Gly
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Arg Ala Asp Ala Ala Pro Thr Val Ser
1               5
```

```
<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 7

Arg Ala Asp Ala Ala Ala Ala Gly Gly Pro Gly Ser
1               5                   10

<210> SEQ ID NO 8
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 8

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 9
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 9

Gly Ser Gly Gly Ser Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

Gly Ser Gly Gly Ser Gly Gly Ser Gly
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 11

Gly Ser Gly Gly Ser Gly Gly Ser Gly Gly Ser Gly
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 12
```

```
Gly Ser Gly Gly Ser Gly Gly Ser Gly Gly Ser Gly Gly Ser Gly
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 13

Gly Ser Gly Gly Ser Gly Gly Ser Gly Gly Ser Gly Gly Ser Gly
1               5                   10                  15

Ser Gly

<210> SEQ ID NO 14
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 14

Gly Ser Gly Gly Ser Gly Gly Ser Gly Gly Ser Gly Gly Ser Gly
1               5                   10                  15

Ser Gly Gly Ser Gly
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 15

Gly Ser Gly Gly Ser Gly Gly Ser Gly Gly Ser Gly Gly Ser Gly
1               5                   10                  15

Ser Gly Gly Ser Gly Gly Ser Gly
            20

<210> SEQ ID NO 16
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 16

Gly Ser Gly Gly Ser Gly Gly Ser Gly Gly Ser Gly Gly Ser Gly
1               5                   10                  15

Ser Gly Gly Ser Gly Gly Ser Gly Gly Ser Gly
            20                  25

<210> SEQ ID NO 17
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 17

Gly Ser Gly Gly Ser Gly Gly Ser Gly Gly Ser Gly Gly Ser Gly
1               5                   10                  15
```

Ser Gly Gly Ser Gly Gly Ser Gly Gly Ser Gly
            20                  25                  30

<210> SEQ ID NO 18
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 18

Gly Gly Ser Gly Gly Ser Gly Gly Ser Gly Gly Ser Gly Gly Ser
1               5                   10                  15

Gly Gly Ser Gly Gly Ser
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 19

Ala Ala Ala Asp Tyr Lys Asp Asp Asp Lys Ile Asp Ala Ala Ala
1               5                   10                  15

Gly Gly Ala Leu Cys Asn
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 20

Ala Ala Ala Asp Tyr Lys Asp Asp Asp Lys Ile Asp Ala Ala Ala
1               5                   10                  15

Gly Gly Ala Leu Cys Asn
            20

<210> SEQ ID NO 21
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 21

Ala Ala Ala Asp Tyr Lys Asp Asp Asp Lys Ile Asp Ala Ala Ala
1               5                   10                  15

Gly Gly Ala Leu Cys Asn Ala Ala Ala Asp Tyr Lys Asp Asp Asp
            20                  25                  30

Lys Ile Asp Ala Ala Ala Gly Gly Ala Leu Cys Asn
            35                  40

<210> SEQ ID NO 22
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 22

Ala Ala Ala Asp Tyr Lys Asp Asp Asp Lys Ile Asp Ala Ala Ala
1               5                   10                  15

Gly Gly Ala Leu Cys Asn Ala Ala Asp Tyr Lys Asp Asp Asp
            20                  25                  30

Lys Ile Asp Ala Ala Ala Gly Gly Ala Leu Cys Asn Ala Ala Asp
        35                  40                  45

Tyr Lys Asp Asp Asp Lys Ile Asp Ala Ala Ala Gly Gly Ala Leu
    50                  55                  60

Cys Asn
65

<210> SEQ ID NO 23
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 23

Ala Ala Ala Asp Tyr Lys Asp Asp Asp Lys Ile Asp Ala Ala Ala
1               5                   10                  15

Gly Gly Ala Leu Cys Asn Ala Ala Asp Tyr Lys Asp Asp Asp
            20                  25                  30

Lys Ile Asp Ala Ala Ala Gly Gly Ala Leu Cys Asn Ala Ala Asp
        35                  40                  45

Tyr Lys Asp Asp Asp Lys Ile Asp Ala Ala Ala Gly Gly Ala Leu
    50                  55                  60

Cys Asn
65

<210> SEQ ID NO 24
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 24

Ala Ala Ala Asp Tyr Lys Asp Asp Asp Lys Ile Asp Ala Ala Ala
1               5                   10                  15

Gly Gly Ala Leu Cys Asn Ala Ala Asp Tyr Lys Asp Asp Asp
            20                  25                  30

Lys Ile Asp Ala Ala Ala Gly Gly Ala Leu Cys Asn Ala Ala Asp
        35                  40                  45

Tyr Lys Asp Asp Asp Lys Ile Asp Ala Ala Ala Gly Gly Ala Leu
    50                  55                  60

Cys Asn Ala Ala Ala Asp Tyr Lys Asp Asp Asp Lys Ile Asp Ala
65                  70                  75                  80

Ala Ala Gly Gly Ala Leu Cys Asn Ala Ala Asp Tyr Lys Asp Asp
            85                  90                  95

Asp Asp Lys Ile Asp Ala Ala Ala Gly Gly Ala Leu Cys Asn
            100                 105                 110

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide

```
<400> SEQUENCE: 25

Ala Glu Ala Ala Ala Lys Ala
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 26

Ala Glu Ala Ala Ala Lys Glu Ala Ala Ala Lys Ala
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 27

Ala Glu Ala Ala Ala Lys Glu Ala Ala Ala Lys Glu Ala Ala Ala Lys
1               5                   10                  15

Ala

<210> SEQ ID NO 28
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 28

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 29
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 29

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 30
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 30

Pro Pro Pro Pro Trp
1               5
```

<210> SEQ ID NO 31
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 31

Pro Pro Pro Pro Pro Trp
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 32

Pro Pro Pro Pro Pro Pro Trp
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 33

Pro Pro Pro Pro Pro Pro Pro Trp
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 34

Pro Pro Pro Pro Pro Pro Pro Pro Trp
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 35

Pro Pro Pro Pro Pro Pro Pro Pro Pro Trp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 36

Pro Pro Pro Pro Pro Pro Pro Pro Pro Pro Trp
1               5                   10

<210> SEQ ID NO 37
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 37

Met Val Pro Cys Thr Leu Leu Leu Leu Ala Ala Ala Leu Ala Pro
1               5                   10                  15

Thr Gln Thr Arg Ala
            20

<210> SEQ ID NO 38
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 38

Met Asp Ser Lys Gly Ser Ser Gln Lys Gly Ser Arg Leu Leu Leu
1               5                   10                  15

Leu Val Val Ser Asn Leu Leu Leu Cys Gln Val Val Ser
            20                  25

<210> SEQ ID NO 39
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 39

Met Arg Gly Thr Pro Leu Leu Leu Val Val Ser Leu Phe Ser Leu Leu
1               5                   10                  15

Gln Asp

<210> SEQ ID NO 40
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 40

Met Ser Ala Leu Leu Ile Leu Ala Leu Val Gly Ala Ala Val Ala Asp
1               5                   10                  15

Tyr Lys Asp Asp Asp Asp Lys Leu
            20

<210> SEQ ID NO 41
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 41

Arg Ile Lys Phe Ser Thr Gly Ser His Cys His Gly Ser Phe Ser Leu
1               5                   10                  15

Ile Phe Leu Ser Leu Trp Ala Val Ile Phe Val Leu Tyr Gln
            20                  25                  30

<210> SEQ ID NO 42
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 42

```
Gly Glu Leu Ser Ser Ser Gly Thr Ser Ser Lys Gly Ile Ile Phe
1               5                   10                  15

Tyr Val Leu Phe Ser Ile Leu Tyr Leu Ile Phe
            20                  25
```

<210> SEQ ID NO 43
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 43

```
Leu Ala Arg Ser Ser Gly Val His Trp Ile Ala Ala Trp Leu Val Val
1               5                   10                  15

Thr Leu Ser Ile Ile Pro Ser Ile Leu Leu Ala
            20                  25
```

<210> SEQ ID NO 44
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 44

```
Ser Gly Thr Thr Ser Gly Thr Thr Arg Leu Leu Ser Gly His Thr Cys
1               5                   10                  15

Phe Thr Leu Thr Gly Leu Leu Gly Thr Leu Val Thr Met Gly Leu Leu
            20                  25                  30

Thr
```

<210> SEQ ID NO 45
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 45

```
Tyr Leu Cys Asn Gly Ala Gly Phe Ala Thr Pro Val Thr Leu Ala Leu
1               5                   10                  15

Val Pro Ala Leu Leu Ala Thr Phe Trp Ser Leu Leu
            20                  25
```

<210> SEQ ID NO 46
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 46

```
Tyr Leu Cys Asn Gly Ala Gly Phe Ala Thr Pro Val Thr Leu Ala Leu
1               5                   10                  15

Val Pro Ala Leu Leu Ala Thr Phe Trp Ser Leu Leu
```

<210> SEQ ID NO 47
<211> LENGTH: 51
<212> TYPE: PRT
<213> ORGANISM: Artificial Sequence
<220> FEATURE:
<223> OTHER INFORMATION: Synthetic polypeptide

<400> SEQUENCE: 47

Arg Asn Ala Val Gly Gln Asp Thr Gln Glu Val Ile Val Val Pro His
1               5                   10                  15

Ser Leu Pro Phe Lys Val Val Ile Ser Ala Ile Leu Ala Leu Val
            20                  25                  30

Val Leu Thr Ile Ile Ser Leu Ile Ile Leu Ile Met Leu Trp Gln Lys
        35                  40                  45

Lys Pro Arg
    50

<210> SEQ ID NO 48
<211> LENGTH: 54
<212> TYPE: PRT
<213> ORGANISM: Artificial Sequence
<220> FEATURE:
<223> OTHER INFORMATION: Synthetic polypeptide

<400> SEQUENCE: 48

Arg Val Ala Val Gly Gln Asp Thr Gln Glu Val Ile Val Val Pro His
1               5                   10                  15

Ser Leu Pro Phe Lys Val Val Ile Ser Ala Ile Leu Ala Leu Val
            20                  25                  30

Val Leu Thr Ile Ile Ser Leu Ile Ile Leu Ile Met Leu Trp Gln Lys
        35                  40                  45

Lys Pro Arg Arg Ile Arg
    50

<210> SEQ ID NO 49
<211> LENGTH: 72
<212> TYPE: PRT
<213> ORGANISM: Artificial Sequence
<220> FEATURE:
<223> OTHER INFORMATION: Synthetic polypeptide

<400> SEQUENCE: 49

Gln Asp Pro Ser Thr Asp Ser Asn Met Glu Thr Thr Val Ile Tyr Val
1               5                   10                  15

Ile Leu Gly Ala Val Ala Met Ile Gly Ala Val Ala Ile Ile Gly Ala
            20                  25                  30

Met Val Ala Val Val Arg Arg Arg Lys Arg Asn Thr Gly Gly Lys Gly
        35                  40                  45

Gly Asp Tyr Ala Pro Ala Pro Gly Arg Asp Ser Ser Gln Ser Ser Asp
    50                  55                  60

Val Ser Leu Pro Asp Cys Lys Ala
65                  70

<210> SEQ ID NO 50
<211> LENGTH: 45
<212> TYPE: PRT
<213> ORGANISM: Artificial Sequence
<220> FEATURE:
<223> OTHER INFORMATION: Synthetic polypeptide

```
<400> SEQUENCE: 50

Gln Asp Ile Ile Leu Tyr Trp Arg Asn Pro Thr Ser Ile Gly Ser Ile
1               5                   10                  15

Val Leu Ala Ile Ile Val Pro Ser Leu Leu Leu Leu Cys Leu Ala
            20                  25                  30

Leu Trp Tyr Met Arg Arg Arg Ser Tyr Gln Asn Ile Pro
        35                  40                  45

<210> SEQ ID NO 51
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 51

Gln Asp Ile Ile Leu Tyr Trp Gly His His Phe Ser Met Asn Trp Ile
1               5                   10                  15

Ala Leu Val Val Ile Val Pro Leu Val Ile Leu Ile Val Leu Val Leu
            20                  25                  30

Trp Phe Lys Lys His Cys Ser Tyr Gln Asp Ile Leu
        35                  40

<210> SEQ ID NO 52
<211> LENGTH: 319
<212> TYPE: PRT
<213> ORGANISM: Artificial Sequence
<220> FEATURE:
<223> OTHER INFORMATION: Synthetic polypeptide

<400> SEQUENCE: 52

Tyr Ala Pro Gly Gly Tyr Asp Ile Met Gly Tyr Leu Ile Gln Ile Met
1               5                   10                  15

Asn Arg Pro Asn Pro Gln Val Glu Leu Gly Pro Val Asp Thr Ser Cys
            20                  25                  30

Ala Leu Ile Leu Cys Asp Leu Lys Gln Lys Asp Thr Pro Val Val Tyr
        35                  40                  45

Ala Ser Glu Ala Phe Leu Tyr Met Thr Gly Tyr Ser Asn Ala Glu Val
    50                  55                  60

Leu Gly Arg Asn Cys Arg Phe Leu Gln Ser Pro Asp Gly Met Val Lys
65                  70                  75                  80

Pro Lys Ser Thr Arg Lys Tyr Val Asp Ser Asn Thr Ile Asn Thr Met
                85                  90                  95

Arg Lys Ala Ile Asp Arg Asn Ala Glu Val Gln Val Glu Val Val Asn
            100                 105                 110

Phe Lys Lys Asn Gly Gln Arg Phe Val Asn Phe Leu Thr Met Ile Pro
        115                 120                 125

Val Arg Asp Glu Thr Gly Glu Tyr Arg Tyr Ser Met Gly Phe Gln Cys
    130                 135                 140

Glu Thr Glu Gly Gly Ser Gly Gly Ser Gly Gly Ser Gly Gly Ser Gly
145                 150                 155                 160

Gly Gly Ser Gly Gly Ser Gly Gly Ser His Thr Leu Tyr Ala Pro Gly
                165                 170                 175

Gly Tyr Asp Ile Met Gly Tyr Leu Ile Gln Ile Met Asn Arg Pro Asn
            180                 185                 190

Pro Gln Val Glu Leu Gly Pro Val Asp Thr Ser Cys Ala Leu Ile Leu
        195                 200                 205
```

```
Cys Asp Leu Lys Gln Lys Asp Thr Pro Ile Val Tyr Ala Ser Glu Ala
    210                 215                 220

Phe Leu Tyr Met Thr Gly Tyr Ser Asn Ala Glu Val Leu Gly Arg Asn
225                 230                 235                 240

Cys Arg Phe Leu Gln Ser Pro Asp Gly Met Val Lys Pro Lys Ser Thr
            245                 250                 255

Arg Lys Tyr Val Asp Ser Asn Thr Ile Asn Thr Ile Arg Lys Ala Ile
            260                 265                 270

Asp Arg Asn Ala Glu Val Gln Val Glu Val Val Asn Phe Lys Lys Asn
                275                 280                 285

Gly Gln Arg Phe Val Asn Phe Leu Thr Ile Ile Pro Val Arg Asp Glu
290                 295                 300

Thr Gly Glu Tyr Arg Tyr Ser Met Gly Phe Gln Cys Glu Thr Glu
305                 310                 315
```

<210> SEQ ID NO 53
<211> LENGTH: 866
<212> TYPE: PRT
<213> ORGANISM: Artificial Sequence
<220> FEATURE:
<223> OTHER INFORMATION: Synthetic polypeptide

<400> SEQUENCE: 53

```
Met Gly Ser Asn Lys Ser Lys Pro Lys Asp Ala Ser Gln Arg Arg Arg
1               5                   10                  15

Ser Leu Glu Pro Ser Glu Asn Val His Gly Ala Gly Gly Ala Phe Pro
            20                  25                  30

Ala Ser Gln Thr Pro Ser Lys Pro Ala Ser Ala Asp Gly His Arg Gly
        35                  40                  45

Pro Ser Ala Ala Phe Val Pro Ala Ala Glu Pro Lys Leu Phe Gly
    50                  55                  60

Gly Phe Asn Ser Ser Asp Thr Val Thr Ser Pro Gln Arg Ala Gly Pro
65                  70                  75                  80

Leu Ala Gly Gly Val Thr Thr Phe Val Ala Leu Tyr Asp Tyr Glu Ser
                85                  90                  95

Arg Thr Glu Thr Asp Leu Ser Phe Lys Lys Gly Glu Arg Leu Gln Ile
            100                 105                 110

Val Asn Asn Thr Glu Gly Asp Trp Trp Leu Ala His Ser Leu Ser Thr
        115                 120                 125

Gly Gln Thr Gly Tyr Ile Pro Ser Asn Tyr Val Ala Pro Ser Asp Ser
130                 135                 140

Ile Gln Ala Glu Glu Trp Tyr Phe Gly Lys Ile Thr Arg Arg Glu Ser
145                 150                 155                 160

Glu Arg Leu Leu Leu Asn Ala Glu Asn Pro Arg Gly Thr Phe Leu Val
                165                 170                 175

Arg Glu Ser Glu Thr Thr Lys Gly Ala Tyr Cys Leu Ser Val Ser Asp
            180                 185                 190

Phe Asp Asn Ala Lys Gly Leu Asn Val Lys His Tyr Lys Ile Arg Lys
        195                 200                 205

Leu Asp Ser Gly Gly Phe Tyr Ile Thr Ser Arg Thr Gln Phe Asn Ser
    210                 215                 220

Leu Gln Gln Leu Val Ala Tyr Tyr Ser Lys His Ala Asp Gly Leu Cys
225                 230                 235                 240

His Arg Leu Thr Thr Val Cys Pro Thr Ser Lys Pro Gln Thr Gln Gly
                245                 250                 255
```

-continued

```
Leu Ala Lys Asp Ala Trp Glu Ile Pro Arg Glu Ser Leu Arg Leu Glu
                260                 265                 270

Val Lys Leu Gly Gln Gly Cys Phe Gly Glu Val Trp Met Gly Thr Trp
            275                 280                 285

Asn Gly Pro Gly Gly Ser Gly Gly Tyr Ala Pro Gly Gly Tyr Asp Ile
        290                 295                 300

Met Gly Tyr Leu Ile Gln Ile Met Asn Arg Pro Asn Pro Gln Val Glu
305                 310                 315                 320

Leu Gly Pro Val Asp Thr Ser Cys Ala Leu Ile Leu Cys Asp Leu Lys
                325                 330                 335

Gln Lys Asp Thr Pro Val Val Tyr Ala Ser Glu Ala Phe Leu Tyr Met
            340                 345                 350

Thr Gly Tyr Ser Asn Ala Glu Val Leu Gly Arg Asn Cys Arg Phe Leu
        355                 360                 365

Gln Ser Pro Asp Gly Met Val Lys Pro Lys Ser Thr Arg Lys Tyr Val
    370                 375                 380

Asp Ser Asn Thr Ile Asn Thr Met Arg Lys Ala Ile Asp Arg Asn Ala
385                 390                 395                 400

Glu Val Gln Val Glu Val Val Asn Phe Lys Lys Asn Gly Gln Arg Phe
                405                 410                 415

Val Asn Phe Leu Thr Met Ile Pro Val Arg Asp Glu Thr Gly Glu Tyr
            420                 425                 430

Arg Tyr Ser Met Gly Phe Gln Cys Glu Thr Glu Gly Gly Ser Gly Gly
        435                 440                 445

Ser Gly Gly Ser Gly Gly Ser Gly Gly Ser Gly Gly Ser Gly Gly Gly
    450                 455                 460

Ser His Thr Leu Tyr Ala Pro Gly Gly Tyr Asp Ile Met Gly Tyr Leu
465                 470                 475                 480

Ile Gln Ile Met Asn Arg Pro Asn Pro Gln Val Glu Leu Gly Pro Val
                485                 490                 495

Asp Thr Ser Cys Ala Leu Ile Leu Cys Asp Leu Lys Gln Lys Asp Thr
            500                 505                 510

Pro Ile Val Tyr Ala Ser Glu Ala Phe Leu Tyr Met Thr Gly Tyr Ser
        515                 520                 525

Asn Ala Glu Val Leu Gly Arg Asn Cys Arg Phe Leu Gln Ser Pro Asp
    530                 535                 540

Gly Met Val Lys Pro Lys Ser Thr Arg Lys Tyr Val Asp Ser Asn Thr
545                 550                 555                 560

Ile Asn Thr Ile Arg Lys Ala Ile Asp Arg Asn Ala Glu Val Gln Val
                565                 570                 575

Glu Val Val Asn Phe Lys Lys Asn Gly Gln Arg Phe Val Asn Phe Leu
            580                 585                 590

Thr Ile Ile Pro Val Arg Asp Glu Thr Gly Glu Tyr Arg Tyr Ser Met
        595                 600                 605

Gly Phe Gln Cys Glu Thr Glu Gly Ser Gly Gly Pro Gly Thr Thr Arg
    610                 615                 620

Val Ala Ile Lys Thr Leu Lys Pro Gly Thr Met Ser Pro Glu Ala Phe
625                 630                 635                 640

Leu Gln Glu Ala Gln Val Met Lys Lys Leu Arg His Glu Lys Leu Val
                645                 650                 655

Gln Leu Tyr Ala Val Val Ser Glu Glu Pro Ile Tyr Ile Val Thr Glu
            660                 665                 670

Tyr Met Asn Lys Gly Ser Leu Leu Asp Phe Leu Lys Gly Glu Thr Gly
```

```
                675                 680                 685
Lys Tyr Leu Arg Leu Pro Gln Leu Val Asp Met Ser Ala Gln Ile Ala
        690                 695                 700

Ser Gly Met Ala Tyr Val Glu Arg Met Asn Tyr Val His Arg Asp Leu
705                 710                 715                 720

Arg Ala Ala Asn Ile Leu Val Gly Glu Asn Leu Val Cys Lys Val Ala
                725                 730                 735

Asp Phe Gly Leu Ala Arg Leu Ile Glu Asp Asn Glu Tyr Thr Ala Arg
            740                 745                 750

Gln Gly Ala Lys Phe Pro Ile Lys Trp Thr Ala Pro Glu Ala Ala Leu
        755                 760                 765

Tyr Gly Arg Phe Thr Ile Lys Ser Asp Val Trp Ser Phe Gly Ile Leu
    770                 775                 780

Leu Thr Glu Leu Thr Thr Lys Gly Arg Val Pro Tyr Pro Gly Met Val
785                 790                 795                 800

Asn Arg Glu Val Leu Asp Gln Val Glu Arg Gly Tyr Arg Met Pro Cys
                805                 810                 815

Pro Pro Glu Cys Pro Glu Ser Leu His Asp Leu Met Cys Gln Cys Trp
            820                 825                 830

Arg Lys Glu Pro Glu Glu Arg Pro Thr Phe Glu Tyr Leu Gln Ala Phe
        835                 840                 845

Leu Glu Asp Tyr Phe Thr Ser Thr Glu Pro Gln Tyr Gln Pro Gly Glu
    850                 855                 860

Asn Leu
865

<210> SEQ ID NO 54
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 54

Pro Xaa Xaa Val His Cys Ser Ala Gly Xaa Gly Arg Thr Gly
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 55

Lys Xaa Xaa Lys Asn Arg Tyr
1               5
```

OPTOGENETIC CONSTRUCT FOR ALLOSTERIC CONTROL OF PROTEIN ACTIVITY

This application claims benefit of priority to U.S. Provisional Patent Application Ser. No. 62/772,841, filed Nov. 30, 2018, the content of which is incorporated herein by reference in its entirety.

This invention was made with government support under grant nos. HL060678 and CA223915, awarded by the National Institutes of Health. The government has certain rights in this invention.

INTRODUCTION

Background

The dysregulation of kinase-mediated phosphorylation of proteins and metabolites is a critical and requisite step in the development and progression of many human malignancies. However, these kinases are also required for the maintenance of physiological cell function. Therefore, the careful dissection of the pathways regulated by such kinases is necessary for the development of targeted antitumor therapies. Methods that enable control of enzyme activity, which require treatment with compounds such as imidazole and rapamycin, have been described (Karginov, et al. (2010) *Nat. Biotechnol.* 28:743-747; Qiao, et al. (2006) *Science* 311:1293-1297). However, these compounds may have additional biological effects and do not allow for repeated cycles of activation/inactivation or subcellular localization.

Optogenetic tools provide a unique combination of advantages enabling precise control of signaling events in time and space. Different light sensitive proteins including light oxygen voltage (LOV) domains, phytochrome B and cryptochrome 2 have been used for engineered regulation of protein interactions in living cells (Zhang & Cui (2015) *Trends Biotechnol.* 33:92-100). These proteins have been suggested for use in studying light-activated protein-protein interactions to mimic ligand-induced dimerization and result in receptor activation (US 2016/0326219). In addition, fusion proteins composed of a protein of interested flanked by photoswitchable photochromic fluorescent protein domains have been described for controlling the activity or localization of selected proteins with light (US 2014/0220615). Further, a White Collar (WC) complex fusion protein composed of WC-1 and WC-2 has been described in connection with regulating gene expression using a light-activated transcription factor (U.S. Pat. No. 6,733,996 B2). In addition, photoreactive domains have been described for regulating interactions by light-controlled steric hindrance (Wu, et al. (2009) *Nature* 461:104-108; Zhou, et al. (2012) *Science* 338:810-814; Mills, et al. (2012) *ACS Synth. Biol.* 1:75-82). However, allosteric regulation of proteins using light-sensitive domains has been challenging due to their structural properties. Activation of kinases by light has been achieved in a few specific cases where kinase signaling can be regulated by its dimerization or changes in localization (Katsura, et al. (2015) *Sci. Rep.* 5:14589; Chang, et al. (2014) *Nat. Commun.* 5:4057; Wend, et al. (2014) *ACS Synth. Biol.* 3:280-285), significantly limiting application of these tools for other kinases. Other approaches that use steric hindrance have been suggested (Zhou, et al. (2017) *Science* 355:836-842). However, the application of this technology for localized activation is technologically cumbersome. Accordingly, novel approaches for light-regulated activation of kinases and other enzymes are needed.

SUMMARY OF THE INVENTION

This invention provides a light-responsive construct composed of a first photoreceptive polypeptide domain and a second photoreceptive polypeptide domain, wherein said first and second photoreceptive polypeptide domains are operatively-linked via a flexible linker and said first and second photoreceptive polypeptide domains are capable of dimerizing with each other. In some embodiments, at least one of the first or second photoreceptive polypeptide domains is a LOV domain of *Neurospora crassa* VIVID protein. In other embodiments, the flexible linker is about 20 to about 100 amino acid residues and optionally includes one or more Gly-Ser-Gly motifs. In certain embodiments, the light-responsive construct further includes flexible linkers configured to operatively-link the first and second photoreceptive polypeptide domains to a protein of interest, e.g., a kinase, phosphatase or recombinase. A composition and polynucleotide encoding the construct are also provided as is a vector and host cell harboring the polynucleotide.

This invention also provides a method of regulating the activity of a protein of interest by inserting into a functional domain of a protein of interest a light-responsive construct comprising a first photoreceptive polypeptide domain and a second photoreceptive polypeptide domain, wherein said first and second photoreceptive polypeptide domains are operatively-linked via a flexible linker and said first and second photoreceptive polypeptide domains are capable of dimerizing with each other thereby producing a fusion protein; and exposing the fusion protein to an effective dose of a light to modulate a conformation of the fusion protein, wherein the modulation of the conformation of the fusion protein regulates the activity of the protein of interest. In some embodiments, at least one of the first or second photoreceptive polypeptide domains is a LOV domain of *Neurospora crassa* VIVID protein. In other embodiments, the flexible linker is about 20 to about 100 amino acid residues and optionally includes one or more Gly-Ser-Gly motifs. In certain embodiments, the protein of interest is a kinase, phosphatase or recombinase. In other embodiments, the activity being regulated is phosphorylation.

This invention further provides a fusion protein composed of a protein of interest having inserted in a functional domain thereof, a light-responsive construct including a first photoreceptive polypeptide domain and a second photoreceptive polypeptide domain, wherein said first and second photoreceptive polypeptide domains are operatively-linked via a flexible linker and said first and second photoreceptive polypeptide domains are capable of dimerizing with each other. In certain embodiments, the protein of interest is a kinase, phosphatase or recombinase.

DETAILED DESCRIPTION OF THE INVENTION

Figure 1:
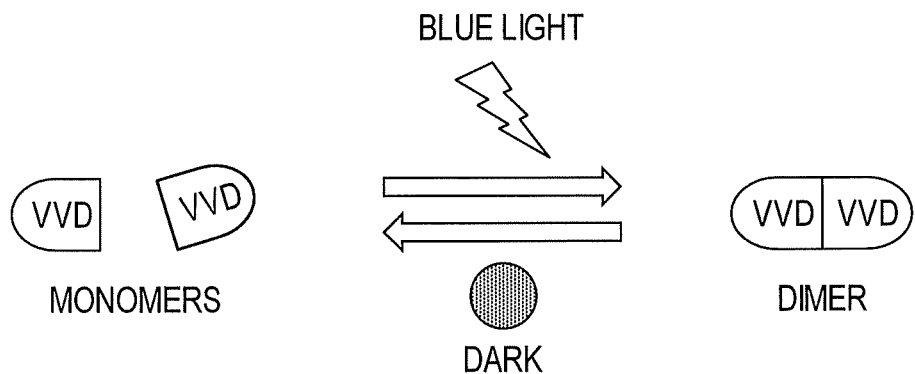
FIG. 1 shows light-induced structural changes in a photoreceptive polypeptide domain of the invention.
Figure 2:
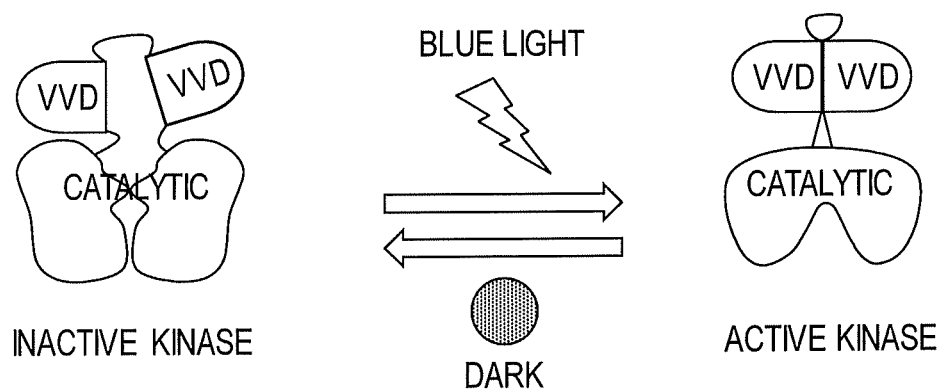
FIG. 2 is a schematic diagram showing regulation of kinases using a light-responsive construct of the invention.

A broadly applicable light-responsive construct and method for optogenetic regulation of kinases, phosphatases and recombinases in living cells has now been developed. To achieve regulation of individual enzymes, a light-sensitive construct (referred to herein as "LightR") is used as an allosteric switch for regulation of activity. In particular, it has been shown that the fungal photoreceptor protein VVD homodimerizes and undergoes significant conformational changes upon illumination with blue light (FIG. 1). Based upon this property of light-sensitive domains such as VVD, a protein "clamp" ("LightR-clamp") composed of a single chain VVD-VVD dimer, has been created that opens in the dark and closes in the light. Insertion of this light-responsive construct into the catalytic domain of a kinase, phosphatase or recombinase causes inactivating distortion in the dark, whereas illumination with blue light releases this distortion thereby rescuing activity (FIG. 2). Advantageously, this approach allows for precise regulation of a variety of proteins as well as individual domains of multidomain proteins. Further, using the light-responsive construct and method of this invention, direct downstream targets of kinase or phosphatase activation in malignant cells can be identified thereby leading to a profound increase in knowledge regarding cancer signaling and the development of novel therapies.

Accordingly, this invention provides a light-responsive construct comprising, consisting essentially of, or consisting of a first photoreceptive polypeptide domain and a second photoreceptive polypeptide domain, wherein said first and second photoreceptive polypeptide domains are operatively-linked via a flexible linker and said first and second photoreceptive polypeptide domains are capable of dimerizing with each other. For the purposes of this invention, the term "construct" refers to a genetically engineered protein that has at least two operatively- or covalently-linked polypeptides, in which one polypeptide comes from a first protein sequence or domain and the other polypeptide comes from a second protein sequence or domain to form a single continuous polypeptide chain, which does not occur in nature. "Protein" and "polypeptide" are used interchangeably herein to refer to a polymer of linearly arranged amino acid residues linked by peptide bonds, whether produced biologically, recombinantly, or synthetically and whether composed of naturally occurring or non-naturally occurring amino acids. Polypeptides of the construct are typically linked via peptide bonds and may be constructed using standard techniques known in the art. In accordance with this invention, the first polypeptide and second polypeptide are linked via a covalent linker, i.e., the construct has the structure: first polypeptide-linker-second polypeptide. The polypeptides that form the construct are typically linked from C-terminal to N-terminal, although they can also be linked from C-terminal to N-terminal, from N-terminal to N-terminal or from N-terminal to C-terminal. The construct polypeptides can be in any order. The term "construct" also refers to conservatively modified variants, polymorphic variants, alleles, mutants, sub-sequences and interspecies homologs of the polypeptides that make up the construct. Constructs can be produced by covalently binding an amino acid chain of a first polypeptide sequence to an amino acid chain of a second polypeptide protein sequence, for example, by preparing a recombinant polynucleotide that contiguously encodes the construct.

A construct is "light-responsive" when the construct changes conformation upon exposure to non-toxic light of a particular wavelength. A "non-toxic light" to which a light-responsive construct responds is light of a discrete wavelength. In some embodiments, the non-toxic light has a wavelength of approximately 450-470 nm. In some embodiments, the light-responsive construct regulates the activity of a protein of interest in the presence of non-toxic light of a particular wavelength. In some embodiments, the construct regulates the activity of a protein of interest in the presence of non-toxic light of a particular wavelength to a greater degree or extent than it regulates the activity of the protein of interest or construct in the absence of the non-toxic light.

The term "light activation" (also referred to herein as "photoactivation") is used herein to refer to control of a protein activity by application of light of selected wavelengths or removal of light from a construct of the invention or protein of interest harboring said construct. The construct or protein of interest is "activated" when light applied to the photoreceptors of the construct causes a change in conformation of the photoreceptors of the construct such that it changes the activity of the construct or a protein of interest harboring said construct. This change is believed to be caused, at least in part, by rotation of the monomeric photoreceptors with respect to each other such that the monomers dimerize and a desired activity of the construct or a protein of interest harboring said construct is changed, e.g., stopped, started, enhanced, or decreased. The term "light activated" (also called "photoactive" in reference to proteins hereof) means a protein capable of being controlled by light to be active or inactive, or more or less active or inactive. Thus, the terms "photoactive proteins" or "photoactivated proteins" also include "photoinactive proteins" or "photoinactivated proteins," respectively.

It is to be understood that the terms "active" and "inactive" in the foregoing explanation are relative and include complete activity of a protein to complete inactivity of the protein (complete "on/off" modes) as well as relative activity or inactivity of the proteins, i.e., the protein can have high activation ratios, low activation ratios, or activation ratios between high and low. In some embodiments, a protein can be controlled by light to have high ratios of activity to inactivity or of inactivity to activity under the control of light of appropriate wavelengths. High ratios are defined herein as ratios of about 2:1 or greater, in embodiments, about 5:1 to about 10:1 or greater. Low ratios are less than about 2:1.

Photoreceptive Polypeptide Domains.

The light-responsive construct of this invention is composed of two photoreceptive polypeptide domains, i.e., a first photoreceptive polypeptide domain and a second photoreceptive polypeptide domain. "Photoreceptive polypeptide domain" refers to a polypeptide domain that, when exposed to one or more pulses of light, results in a conformational change of the polypeptide domain and hence a light-responsive construct containing the same. As used herein, the terms "domain" and "region" are used interchangeably herein and refer to a contiguous sequence of amino acids within a protein of interest, typically characterized by being either conserved or variable and having a defined function, such as being affected by non-toxic light of a particular wavelength, conferring stability or instability, enzymatic function, etc.

In accordance with the light-responsive construct of this invention, the first and second photoreceptive polypeptide domains are capable of dimerizing with each other. The expression "capable of dimerizing" or "capable of dimerization upon excitation" is intended to indicate that the first and second photoreceptive polypeptide domains can non-covalently interact to form a macromolecular complex. Accordingly, the first and second photoreceptive polypeptide domains are covalently linked at the primary sequence level and non-covalently interact at a quaternary level, in particular upon exposure to light.

In some aspects, the first and second photoreceptive polypeptide domains are the same. In other aspects, the first and second photoreceptive polypeptide domains are different. Accordingly, this invention provides for both homodimers and heterodimers.

Photoreceptive polypeptide domains that function in a light-dependent manner, for instance, by changing structure in response to exposure to light, include any domain with a chromophore, which is capable of detecting or capturing light energy. For example, engineered or naturally occurring photoreceptors that absorb photons and have a resulting conformational change are known in the art and can be used in compositions and methods of the invention. Examples of a variety of natural and engineered photoreceptors are described by Harper (2003) *Science* 301:1541-1544; Yao, et al. (2008) *Nat. Chem. Biol.* 4:491-497; Möglich & Moffat (2010) *Photochem. Photobiol. Sci.* 9(10):1286-300; Salomon, et al. (2000) *Biochem.* 39:9401-9410; Christie, et al. (2007) *Biochem.* 46:9310-9319; Zoltowski, et al. (2009) *Nat. Chem. Biol.* 5(11):827-34; Miesenbock (2011) *Annu. Rev. Cell, Dev. Biol.* 27:731-758; Losi & Gartner (2012) *Annu. Rev. Plant Biol.* 63:49-72; and Losi & Gartner (2011) *Photochem. Photobiol.* 87:491-510. Non-limiting examples of photoreceptive polypeptide domains that can be used in the light-responsive construct described herein include a Light-Oxygen-Voltage (LOV) photoreceptor domain, a LOV2 photoreceptor domain, a Cryptochrome (CRY) photoreceptor domain, Blue-light-using FAD (BLUF) photoreceptor domain, a Phytochrome (PHY) photoreceptor domain, CIBN (N-terminal domain of CIB1 (cryptochrome-interacting basic-helix-loop-helix protein 1)), PIF (phytochrome interacting factor), FKF1 (Flavin-binding, Kelch repeat, F-box 1), GIGANTEA, Dronpa, VIVID (VVD), EL222 and a UVR8 photoreceptor domain.

The "light-oxygen-voltage-sensing" or "LOV" domain superfamily is a group of light-sensing domains that bind flavins as prosthetic groups and act as reversible photoswitches in bacteria, fungi and plants. When exposed to blue light (440-473 nm) LOV domains undergo a conformational change, leading to allosteric control of effector domains. An exemplary LOV domain includes residues 180 to 312 of *Ochromonas danica* aureochrome 1 like protein (Uniprot Accession No. C5NSW6). Another LOV domain of use in the invention is located at the C-terminus of a aureochrome 1 of *Vaucheria frigida* (Takahashi, et al. (2007) *Proc. Natl. Acad. Sci. USA* 104 49):19625-30). Additional LOV domains are described in U.S. Pat. No. 9,279,769 B2, which are incorporated herein by reference.

"Cryptochrome" or "CRY" is an ultraviolet-A/blue light photoreceptor found in plants, insects, fish, amphibians, mammals and fungi. Cryptochromes are composed of two major domains, the N-terminal PHR (for Photolyase-Homologous Region) and the C-terminal extension CCE (for Cryptochrome C-terminal Extension) domain. The PHR domain is required for chromophore-binding and homodimerization (Sang, et al. (2005) *Plant Cell* 17:1569-84; Yu, et al. (2007) *Proc. Natl. Acad. Sci. USA* 104:7289-94), whereas CCE is an effector domain of cryptochrome (Yang, et al. (2000) *Cell* 103:815-827; Wang, et al. (2001) *Science* 294: 154-158). CRY proteins are known in the art and include those obtained from, e.g., *Chlamydomonas reinhardtii*, *Physcomitrella patens* (GENBANK Accession No. XP 001751763), *Adiantum capillus-veneris*, *Arabidopsis thaliana* (GENBANK Accession Nos. NP_567341 and NP_171935), *Lycopersicon esculentum* (GENBANK Accession No. NP_001234667), *Sorghum bicolor* (GENBANK Accession Nos. XP 002436988 and AAV97867), *Oryza sativa* (GENBANK Accession Nos. BAD17529 and BAD23780), *Glycine max* (GENBANK Accession Nos. NP_001242152 and NP_001235220) and *Sinapis alba* (Lin & Todo (2005) *Genome Biology* 6:220). A CRY of this invention may be composed of the PHR and CCE domains or only the PHR domain which has shown to be sufficient for light-dependent conformational changes (WO 2019/084362). While CRY-CRY homodimers are contemplated, a CRY-CIBN heterodimer is also included within the scope of this invention (see Liu, et al. (2008) *Science* 322(5907): 1535-9).

The phytochromes (PHY) include a family of biliprotein photoreceptors that enable plants to adapt to their prevailing light environment. PHY domains are excitable by red light, i.e., by light having a wavelength in the range of 600-690 nm, preferably 610-680 nm, more preferably in the range of 620-670 nm, and most preferably in the range of 630-660 nm, such as by light having a wavelength of about 650 nm. In addition, the light sensing PHY domain can be inactivated by light with a wavelength in the range of 700-750 nm, preferably 710-740 nm, more preferably 720-730 nm. Phytochromes from cyanobacteria, to green algae and higher plants are composed of a well conserved N-terminal domain, roughly 390-600 amino acids in length (see, e.g., U.S. Pat. No. 6,046,014), to which the phytobilin prosthetic group is bound. An exemplary phytochrome sequence is disclosed in US 2003/0082809. Additional Phy proteins include *Arabidopsis* PhyA provided under GENBANK Accession No. NM_001123784 and PhyB provided under GENBANK Accession No. NM_127435. While PHY-PHY homodimers are contemplated, a PHY-PIF heterodimer is also included with in the scope of this invention (see WO 2013/133643; Kim, et al. (2014) *Chem. Biol.* 21:903-912).

"CIBN" as used herein refers to the N-terminus of CIB that interacts with cryptochrome (CRY) upon irradiation with light. As used herein, "CIB" refers to cryptochrome-interacting basic-helix-loop-helix protein and is represented by the *Arabidopsis* CIB1 provided under GENBANK Accession No. NM_119618.

As used herein, "PIF" refers to a phytochrome interacting factor, which is represented by the *Arabidopsis* PIF1, PIF3, PIF4, PIF5, PIF6, or PIF7 proteins respectively provided under GENBANK Accession Nos. NM_001202630, NM_179295, NM_180050, NM_180690, NM_001203231, and NM_125520.

"FKF" refers to Flavin-binding, Kelch repeat, F-box proteins, typically FKF1 (GENBANK Accession No. NM_105475) of *Arabidopsis*.

Dronpa refers to a refers to photoreceptive polypeptide from a coral of the genus Pectiniidae. Dronpa rapidly converts between a dark state and a bright state upon illumination with 490 nm and 400 nm light, respectively. Therefore, Dronpa mutants that either dimerize in the bright state but remain monomeric in the dark state have been generated and fused to proteins such as a guanine nucleotide exchange factor (GEF) or protease (Zhou, et al. (2013)

*Science* 338(6108):810-4). When in the bright state, the two Dronpa domains form an interface and upon exposure to 400 nm light, the interface breaks. Representative Dronpa are provided under GENBANK Accession Nos. AB180726, ADE48854, and BAD72874.1.

The EL222 protein is a protein composed of a photosensory (LOV) domain, an interdomain linker (Jα-helix), and a helix-turn-helix (HTH) DNA binding domain. In the dark, the LOV domain binds the HTH domain via interactions of its β-sheet with the HTH Illumination with blue light triggers a photochemical reaction between the LOV domain and its flavin chromophore that leads to conformational changes that disrupt the LOV-HTH domain interactions and expose the HTH 4α-helix. The HTH 4α-helix then binds to another HTH on a second EL222 molecule generating an EL222 dimer.

"UVR8" is a seven-bladed 3-propeller protein of 440 amino acid residues in length (Christie, et al. (2012) *Science* 335:1492-1496; Wu, et al. (2012) *Nature* 484:214-219). Molecular and biochemical studies have demonstrated that in light conditions devoid of UV-B, the UVR8 photoreceptor exists as a homodimer, which undergoes instant monomerization following UV-B exposure, a process dependent on an intrinsic tryptophan residue that serves as an UV-B chromophore (Rizzini, et al. (2011) *Science* 332:103-106). Accordingly, in some embodiments, dimerization is induced in the absence of UV-B light. Alternatively, when used in combination with COP1, a light-induced UVR8-COP1 heterodimer can be formed (Rizzini, et al. (2011) *Science* 332:103-106; Crefcoeur, et al. (2013) *Nat. Commun.* 4:1779).

In certain aspects of this invention, the first and/or second photoreceptive polypeptide domain of the light-responsive construct is the VIVID (VVD) protein of *Neurospora crassa*, or a mutant thereof. VVD is a light-sensitive protein involved in the blue-regulated cell signaling pathway. Under blue light, it can react with flavin adenine dinucleotide (FAD, Flavin Adenine Dinucleotide) to form a dimer. The full-length VVD protein contains 186 amino acids and contains only one light-sensitive LOV domain. Studies have shown that the VVD protein lacking the N-terminal 36 amino acid residues (VVD36) is more stable than the full-length protein. In addition, VVD mutants Ile74Val and Ile85Val have been shown to facilitate dissociation of VVD dimers when placed in the dark (Zoltowski, et al. (2009) *Nat. Chem. Biol.* 5:827-834). This enables faster reversibility of light-mediated changes. Mutations of Met135 and Met165 to Ile strengthen dimer binding (Zoltowski, et al. (2009) *Nat. Chem. Biol.* 5:827-834). These mutants have been used previously to fine-tune light-mediated regulation of VVD dimerization (Zoltowski, et al. (2009) *Nat. Chem. Biol.* 5:827-834; Kawano, et al. (2015) *Nat. Commun.* 6:6256). Accordingly, one or more of these mutations may be introduced into the VVD sequence to modulate the kinetics of light activation. Representative VVD proteins of use in this invention are provided under UniProtKB Accession No. Q1K5Y8, GENBANK Accession No. XP 957606 and SEQ ID NO:1. In certain embodiments, at least one of the photoreceptor domains comprises, consists essentially of or consists of residues His37 to Glu184 of SEQ ID NO:1. In other embodiments, at least one of the photoreceptor domains comprises, consists essentially of or consists of residues Tyr40 to Glu186 of SEQ ID NO:1. In further embodiments, at least one of the photoreceptor domains comprises, consists essentially of or consists of residues Tyr37 to Glu186 of SEQ ID NO:1. In yet other embodiments, the photoreceptor domains include the LOV domain of VIVID having one or more of the following amino acid substitutions: Ile74Val, Ile85Val, Met135Ile, or Met165Ile.

Derivatives and analogs of the photoreceptive polypeptide domains are all contemplated and can be made by altering their amino acid sequences by substitutions, additions, and/or deletions/truncations or by introducing chemical modifications that result in functionally equivalent polypeptides. It will be understood by one of ordinary skill in the art that certain amino acids in a sequence of any polypeptide may be substituted for other amino acids without adversely affecting the activity of the polypeptides.

When expressed in a cell or membrane, the construct of the invention can be activated by exposure to light having a pulse length, irradiance level, and wavelength suitable to activate the first and/or second photoreceptor polypeptide domains. Selection of the wavelength can be based in part, on the identity of the photoreceptor polypeptide domains included in the construct. In certain embodiments, the a photoreceptive polypeptide domain responsive to blue light, e.g., the VVD polypeptide photoreceptor, may be modulated by contacting the photoreceptor polypeptide with blue light having a wavelength of least 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, or 500 nm, including all wavelengths in the range. It is understood that a wavelength of light suitable to modulate a photoreceptor in a construct of the invention may be any wavelength that is determined to modulate that photoreceptor. Various means to determine a suitable wavelength with which to modulate a photoreceptor, as well as suitable wavelengths for use with specific photoreceptors are known in the art and can be used in conjunction with the teaching provided herein to select and confirm a wavelength of light for use in methods of the invention.

Parameters of a dose of light with which a construct of the invention is contacted or exposed to may also include the light's irradiance and pulse frequency in addition to the light's wavelength. In certain embodiments of the invention, the irradiance in a dose of light with which a construct of the invention is contacted to modulate the construct is between 2 and 500 microwatts/mm$^2$ including every value within the listed range. In certain embodiments, the photoreceptive polypeptide domains of the construct may be activated by contact with as little as 10 µW/mm$^2$. In other embodiments of the invention, a dose of light with which a construct of the invention is contacted to modulate the photoreceptive polypeptide domains of the construct may be delivered as a continuous pulse or at a pulse frequency from 1 Hz to 20 kHz including every value within the range. In certain embodiments at least 1, 2, 3, 4, 5, 6, 7, 8, 9, 10, 15, 20, 30, 50, 100, 200, 300, 400, 500, 600, 700, 800, 900, 1000, or more pulses of light (including all numbers within the listed range) may be included in a dose of light that is applied to a photoreceptor domain of a construct of the invention.

It will be understood that the photoreceptor polypeptides listed herein are not intended to be limiting and that alternative photoreceptor polypeptide sequences may be included in a construct of the invention. Additional photoreceptor polypeptides (and sequences thereof) are known in the art and may be included in a construct of the invention.

Linkers.

In certain aspects of this invention, the first photoreceptive polypeptide domain and second photoreceptive polypeptide domain of the construct of this invention are operatively-linked via a flexible linker. A linker of the present invention serves the purpose of covalently attaching the first photoreceptive polypeptide domain to the second photoreceptive polypeptide domain. A "flexible linker" refers to a linker that covalently attaches the first photoreceptive polypeptide domain to the second photoreceptive polypeptide domain at a distance appropriate for the first and second photoreceptive polypeptide domains to move freely relative to one another and dimerize. The flexible linker of this invention may be a peptide linker or other type of chemical linker (e.g., a carbohydrate linker, a lipid linker, a fatty acid linker, or a polyether linker such as PEG). See, for example, Hermanson (2013) Bioconjugate Techniques, 3rd Ed. Academic Press. In certain embodiments, the linker is a peptide linker.

Peptide linkers of use in this invention can be as few as 5 amino acids in length, or 10 amino acids in length or 20 amino acids in length; or as many as 75 amino acids in length, 85 amino acids in length or 100 amino acids in length. The linker length may further be present within any range delimited by any pair of the foregoing values, such as between 20 and 75 amino acid residues, or between 10 and 85 amino acid residues, for example. Ideally, the flexible linker linking the photoreceptive polypeptide domains is about 20 to about 100 amino acid residues in length, or more preferably about 20 to about 100 amino acid residues in length. Flexible peptide linkers have conventionally included glycine and optionally serine residues. By way of illustration, a flexible linker can be based upon a (GGGGS)$_n$ (SEQ ID NO:2) motif (Chen, et al. (2013) Adv. Drug Deliv. Rev. 65:1357-69), wherein n is 5, 10, 15, or 20 resulting in a linker of 5, 50, 75 and 100 amino acids in length, respectively. Other linkers including glycine and serine can be based upon a (G)$_n$, (GS)$_n$, (GGSG)$_n$ (SEQ ID NO:3), (GSG)$_n$ or (SAGG)$_n$ (SEQ ID NO:4) motif. In accordance with these linkers, n is in the range of 1 to 15. Other flexible linkers include, but are not to, homoglycine, SAKTTPKLGG (SEQ ID NO:5) or variants thereof, RADAAPTVS (SEQ ID NO:6) and variants thereof such as RADAAAAGGPGS (SEQ ID NO:7) and RADAAAA (G$_4$S)$_4$ (SEQ ID NO:8). Exemplary flexible linkers include, but are not limited to, GSGGSG (SEQ ID NO:9), GSGGSGGSG (SEQ ID NO:10), GSGGSGGSGGSG (SEQ ID NO:11), GSGGSGGSGGSGGSG (SEQ ID NO:12), GSGGSGGSGGSGGSGGSG (SEQ ID NO:13), GSGGSGGSGGSGGSGGSGGSG (SEQ ID NO:14); GSGGSGGSGGSGGSGGSGGSGGSG (SEQ ID NO:15), GSGGSGGSGGSGGSGGSGGSGGSGGSG (SEQ ID NO:16), or GSGGSGGSGGSGGSGGSGGSGGSGGSGGSG (SEQ ID NO:17). In certain embodiments, the flexible linker includes one or more GSG motifs. In further embodiments, the flexible linker linking the first and second photoreceptive polypeptide domains consists of the amino acid sequence GGSGGSGGSGGSGGGSGGSGGS (SEQ ID NO:18).

In some embodiments, a linker of the construct may include a FLAG® tag. An example of a linker that includes a FLAG® tag has the motif (AAADYKDDDDKIDAAAGGALCN)$_n$ (SEQ ID NO:19), and can include, e.g., AAADYKDDDDKIDAAAGGALCN (SEQ ID NO:20), AAADYKDDDDKIDAAAGGALCNAAADYKDDDDKIDAAAGGALCN (SEQ ID NO:21), AAADYKDDDDKIDAAAGGALCNAAADYKDDDDKIDAAAGGALCNAAADYKDDDDKIDAA AGGALCN (SEQ ID NO:22), AAADYKDDDDKIDAAAGGALCNAAADYKDDDDKIDAAAGGALCNAAADYKDDDDKIDAA AGGALCN (SEQ ID NO:23), or AAADYKDDDDKIDAAAGGALCNAAADYKDDDDKIDAAAGGALCNAAADYKDDDDKIDAA AGGALCNAAADYKDDDDKIDAAAGGALCNAAADYKDDDDKIDAAAGGALCN (SEQ ID NO:24).

In certain embodiments of the invention, a linker of the construct may be a helical-type linker. An example of a helical-type linker that may be used in a construct of the invention includes, but is not limited to, A(EAAAK)$_n$A (SEQ ID NO:25). In accordance with these linkers, n is 2, 3, 4 or 5. Specific examples of helical-type linkers include AEAAAKEAAAKA (SEQ ID NO:26), AEAAAKEAAAKEAAAKA (SEQ ID NO:27), AEAAAKEAAAKEAAAKEAAAKA (SEQ ID NO:28), and AEAAAKEAAAKEAAAKEAAAKEAAAKA (SEQ ID NO:29).

In other embodiments, a linker of the construct is a Type II polyproline helix linker. An example of a Type II polyproline helix linker that may be used in a construct of the invention includes, but is not limited to, (P)$_n$-W. In accordance with these linkers, n is 1, 2, 3, 4, 5, 6, 7, 8, 9, or 10. Specific examples of Type II polyproline helix linker include PPPPW (SEQ ID NO:30), PPPPPW (SEQ ID NO:31), PPPPPPW (SEQ ID NO:32), PPPPPPPW (SEQ ID NO:33), PPPPPPPPW (SEQ ID NO:34), PPPPPPPPPW (SEQ ID NO:35), or PPPPPPPPPPW (SEQ ID NO:36).

It is understood that the linkers listed herein are not intended to be limiting and that additional linkers may be included in the construct of the invention. Additional linkers (and sequences thereof) are well known in the art and may be included in a construct of the invention. See, for example, US 2006/0057614; Ibanez-Tallon, et al. (2004) Neuron 43:305-311; Holford, et al. (2009) Front. Mol. Neurosci. 2:21; Fortin, et al. (2009) Proc. Natl. Acad. Sci. USA 106:8049-8054; Auer, et al. (2010) Nat. Meth. 7:229-236; Stürzebecher, et al. (2010) J. Physiol. (Lond.) 588:1695-1707; and Best, et al. (2007) Proc. Natl. Acad. Sci. USA 104:18964-18969. Routine methods of selecting and optimizing linker based on length, flexibility, etc. are described in George & Heringa (2002) Protein Engineering 15:871-879.

Fusion Proteins.

Insertion of the construct of this invention into the catalytic domain of a kinase, phosphatase or recombinase has been shown to cause inactivating distortion in the dark, whereas exposure to light releases this distortion thereby rescuing activity. Accordingly, this invention further provides a fusion protein composed of a protein of interest (e.g., an enzyme, a receptor, transcription factor, or channel) including an insertion of, at an internal position, a light-responsive construct composed of a first photoreceptive polypeptide domain and a second photoreceptive polypeptide domain, wherein said first and second photoreceptive polypeptide domains are operatively-linked via a flexible linker and said first and second photoreceptive polypeptide domains are capable of dimerizing with each other. Insertion of the light-responsive construct can be directly (e.g., as an in-frame fusion between the amino acids of the protein of interest and the N- and C-terminus of the construct) or indirectly (e.g., via linkers that covalently attach the amino acids of the protein of interest to the N- and C-terminus of the construct). Accordingly, in certain embodiments, the light-responsive construct further includes flexible linkers configured to operatively-link the first and second photoreceptive polypeptide domains of the construct to a protein of interest. Alternatively stated, the construct has a flexible linker attached to the N- and/or C-terminal end. By way of illustration, a construct with additional flexible linkers would have the structure: $L_1$-$PPD_1$-$L_2$-$PPD_2$-$L_3$, wherein L is a linker, PPD is a photoreceptive polypeptide domain, each of $L_1$, $L_2$ and $L_3$ are the same or different and $PPD_1$ and $PPD_2$ form a heterodimer or homodimer. Flexible linkers of use in this aspect of the invention are disclosed elsewhere herein. In some embodiments, the flexible linkers configured to link the construct to the protein of interest are about 5 to about 100 amino acid residues in length, or more preferably about 20 to about 100 amino acid residues in length.

The protein of interest in the fusion protein of the invention can be any known protein of interest. The term "protein of interest" encompasses full length proteins, modified proteins, fragments of proteins, and functional domains of proteins. In one embodiment, the protein of interest is a mammalian protein, e.g., a human protein. In one embodiment, the protein of interest or a functional fragment thereof is selected from a family of proteins, e.g., kinases, phosphatases, recombinases, GTPases (such as Rac1 and Cdc42), guanine nucleotide exchange factors, proteases, transcription factors, integrins, cytoskeletal proteins (e.g., actin and microtubule proteins), receptors, transport channels, nucleases (e.g., integrases, invertases, and resolvases) and cytoskeleton-associated proteins that are critical in regulation of dynamics (e.g., components of Arp2/3 complex, fascin, cofilin, Ena/VASP and other capping proteins). In particular embodiments, the protein of interest is an enzyme. In certain embodiments, the protein of interest is a kinase, phosphatase or recombinase. In particular embodiments, the protein of interest is a tyrosine kinase. Tyrosine kinases include receptor tyrosine kinases (RTKs) as well as non-receptor tyrosine kinases (nRTKs).

RTKs are the high-affinity cell surface receptors for many polypeptide growth factors, cytokines, and hormones. RTKs have been shown to be key regulators of normal cellular processes as well as to have a critical role in the development and progression of many types of cancer. RTKs of particular use in the present invention include, but are not limited to, EGF receptors (such as EGFR/ErbB1, ErbB2, ErbB3 or ErbB4), FGF receptors, RET receptors, insulin receptors, PDGF receptors, VEGF receptors, HGF receptors, Trk receptors, Eph receptors, AXL receptors, LTK receptors, TIE receptors, ROR receptors, DDR receptors, KLG receptors, RYK receptors, and MuSK receptors, more preferably from EGF receptors, FGF receptors and RET receptors, and most preferably from EGFR, FGFR1 and RET.

Non-receptor tyrosine kinases (nRTKs) are cytosolic enzymes that are responsible for catalyzing the transfer of a phosphate group from a nucleoside triphosphate donor, such as ATP, to tyrosine residues in proteins. nRTKs of particular use in the present invention include, but are not limited to, the Src family of nRTKs (e.g., SRC, FGR, FYN, YES1, BLK, HCK, LCK and LYN), the Abl (Abelson murine leukemia viral oncogene homolog) family of nRTKs (e.g., ABL1 and ARG), the Ack (Activated CDC42 kinase) family of nRTKs (e.g., ACK1 and TNK1), the Csk (C-terminal Src kinase) family of nRTKs (e.g., CSK and MATK), the Fak (focal adhesion kinase) family of nRTKs (e.g., FAK and PYK2), the Fes (Feline sarcoma oncogene) family of nRTKs (e.g., FES and FER), the Frk (Fyn-related kinase) family of nRTKs (e.g., FRK, BRK and SRMS), the Jak (Janus kinase) family of nRTKs (e.g., JAK1, JAK2, JAK3 and TYK2), the Tec family of nRTKs (e.g., TEC, BMX, BTK, ITK and TXK), and the Syk (Spleen tyrosine kinase) family of nRTKs (e.g., SYK and ZAP10).

Protein phosphatases remove a phosphate group from the phosphorylated amino acid residue of its substrate. Protein phosphatases include tyrosine-specific phosphatases, serine/threonine-specific phosphatases, dual specificity phosphatases, and histidine phosphatases. Tyrosine-specific phosphatases are key regulatory components in signal transduction pathways (such as the MAP kinase pathway) and cell cycle control, and are important in the control of cell growth, proliferation, differentiation, transformation, and synaptic plasticity. Accordingly, in some aspects of this invention, the protein phosphatase is a tyrosine-specific phosphatase (PTPase). PTPases carry a highly conserved active site motif, employ a common catalytic mechanism, and possess a similar core structure made of a central parallel beta-sheet with flanking alpha-helices containing a beta-loop-alpha-loop that encompasses the PTP signature motif. As with the tyrosine kinases, PTPases include receptor tyrosine phosphatases and non-receptor tyrosine phosphatases. Examples of receptor tyrosine phosphatases include, but are not limited to, PTPRA, PTPRB, PTPRC, PTPRD, PTPRE, PTPRF, PTPRG, PTPRH, PTPRJ, PTPRK, PTPRM, PTPRN, PTPRO, PTPRQ, PTPRR, PTPRS, PTPRT, PTPRU and PTPRZ. Non-receptor tyrosine phosphatases include, but are not limited to, PTPN1 (PTP1B), PTPN2, PTPN3, PTPN4, PTPN5, PTPN6, PTPN7, PTPN9, PTPN11 (SHP2), PTPN12 (PTP-PEST), PTPN13, PTPN14, PTPN18, PTPN20, PTPN20CP, PTPN21, PTPN22 and PTPN23. In particular embodiments, the protein of interest is PTPN1, PTPN11 or PTP12.

Recombinase are enzymes that promote genetic recombination. Recombinases can be used to control gene expression and can include excision/insertion, inversion, translocation and cassette exchange, which have been used individually or combined in a wide range of configurations to control gene expression. Examples of recombinases that can be included in a fusion protein of this invention include Cre recombinases, Hln recombinases, Tre recombinases and FLP recombinases. In particular embodiments, the recombinase of the fusion protein of this invention is a Cre recombinase. Cre recombinase is a tyrosine recombinase. The enzyme uses a topoisomerase I-like mechanism to carry out site-specific recombination events between two loxP sites leading to deletion or gene conversion.

To inactivate a protein of interest, the construct of this invention is preferably inserted into a functional domain of the protein of interest. The functional domain of the protein of interest may be selected from a translocation signal (such as a nuclear localization signal, nuclear export signal, or organelle targeting domain); a binding domain; an activation loop of a kinase; the catalytic domain of a proteinase, kinase, or other enzyme; the ATP binding pocket of a kinase or other enzyme; the regulatory domain of a kinase or other enzyme (e.g., the RI or RII domain of protein kinase A); the regulatory light chain and/or the ATPase domain of a myosin motor protein, the regulatory light chain and/or the ATPase domain of a microtubule-driven motor protein, and an SH (Src Homology) domain. In particular aspects, insertion of the light-responsive construct is at an amino acid residues located in a loop or domain at the surface of the protein of interest.

In one aspect, the light-responsive construct is inserted into the catalytic domain of an enzyme. In this respect, the modified enzyme would have the structure: $E(CD_1)$-$L_1$-$PPD_1$-$L_2$-$PPD_2$-$L_3$-$E(CD_2)$, wherein $CD_1$ and $CD_2$ are respectively the N- and C-terminal portions of the catalytic domain of enzyme (E), L is a linker, PPD is a photoreceptive polypeptide, domain, each of $L_1$, $L_2$ and $L_3$ are the same or different and $PPD_1$ and $PPD_2$ form a heterodimer or homodimer. As is known in the art, the "catalytic domain" of an enzyme is the region of the enzyme that causes the enzymatic reaction. The catalytic domain of numerous enzymes are well-known to those having ordinary skill, and can be readily identified by crystal structure analysis and/or sequence analysis using, e.g., the NCBI Conserved Domain Database (Marchler-Bauer, et al. (2017) *Nucl. Acids Res.* 45:D200-D203), SCOPEC (George, et al. (2004) *Bioinformatics* 20:i130-1136) or GASS-WEB (Moraes, et al. (2017) *Nucl. Acids Res.* 45:W315-W319). Ideally, insertion of the light-responsive construct does not interfere with substrate binding. In some embodiments, the light-responsive construct is inserted into the catalytic domain of a kinase, phosphatase or recombinase. In particular embodiments, the light-responsive construct is inserted into the catalytic domain of a tyrosine kinase. In certain embodiments, the light-responsive construct is inserted into the catalytic domain of a nRTK. In specific embodiments, the light-responsive construct is inserted into the catalytic domain of cSrc, Abl or PKA. Insertion of the construct into the catalytic domain of a protein kinase, phosphatase or recombinase provides an allosteric switch for regulation of the kinase, phosphatase or recombinase.

In another aspect, the light-responsive construct is inserted into the activation loop of a kinase. The activation loop of a kinase is a flexible loop located proximal to the catalytic domain. Most kinases are activated by phosphorylation of specific residues in the activation loop, which then counteract the positive charge of the arginine in the catalytic domain HRD motif. In particular embodiments, the light-responsive construct is inserted into the activation loop of a tyrosine kinase. In certain embodiments, the light-responsive construct is inserted into the activation loop of a nRTK. In specific embodiments, the light-responsive construct is inserted into the activation loop of cSrc. Ideally, insertion of the light-responsive construct into the activation loop of a kinase will provide for modulation of the phosphorylation of the kinase.

Additional Elements of the Light-Responsive Construct and/or Fusion Protein.

In certain embodiments, the construct/fusion protein of the invention may include a signal polypeptide domain. A signal polypeptide domain may be a polypeptide including a trafficking signal that assists in the direction and/or delivery of a construct/fusion protein of the invention to a particular location within or external to a cell in which it is expressed. In certain embodiments, a trafficking signal is a polypeptide sequence that assists in locating or directing a construct/fusion protein of the invention to an internal cell structure such as the interior surface of the plasma membrane or to an internal cell membrane such as, but not limited to, a mitochondrial membrane, an endoplasmic reticular membrane, a nuclear membrane, etc. Thus, in certain embodiments, a trafficking sequence may be a mitochondrial targeting sequence (MTS), an ER targeting sequence, etc. Internal cell membrane targeting sequences and their use in constructs are well-known in the art.

In certain embodiments, a trafficking signal that is included in a construct/fusion protein of the invention is a secretion signal. A secretion signal of use in this invention may include a polypeptide derived from a truncated MHC I antigen (ss) polypeptide, a prolactin (prl) polypeptide, an achR beta subunit (acr) polypeptide, or a serine protease I (sr1) polypeptide. In certain embodiments, the construct/fusion protein includes a truncated MHC I antigen polypeptide. Non-limiting examples secretion signals include a truncated MHC I antigen secretion signal polypeptide having the amino acid sequence MVPCTLLLL-LAAALAPTQTRA (SEQ ID NO:37), a prolactin secretion signal polypeptide having the amino acid sequence MDSKGSSQKGSRLLLLLVVSNLLLCQVVS (SEQ ID NO:38), a AchR beta subunit secretion signal polypeptide having the amino acid sequence MRGTPLLLVVSLF-SLLQD (SEQ ID NO:39), or a derivative thereof. In still other embodiments, a construct/fusion protein may include a secretion signal of a Serine protease I polypeptide with a FLAG® tag. A non-limiting example of a Serine protease I with a FLAG®, which is also referred to herein as "sr1," is set forth herein as MSALLILALVGAAVADYKDDDDKL (SEQ ID NO:40), or a derivative thereof.

It is understood that the trafficking signal sequences, including intracellular and secretion signal polypeptides listed herein are not intended to be limiting and that additional trafficking signal sequences, such as intracellular and secretion signal polypeptides (and sequences thereof), etc. are well-known in the art and may be included in a construct/fusion protein of the invention. Methods of selecting and optimizing trafficking signal sequences for localization of polypeptide sequences in a cell, membrane, etc. are routine in the art. See, for example, Emanuelsson, et al., (2000) *J. Mol. Biol.* 300:1005-1016.

In certain embodiments of the invention, the construct/fusion protein of the invention may include a membrane-anchoring signal polypeptide domain. In certain embodiments of the invention, a membrane-anchoring polypeptide domain anchors other construct domains to a plasma membrane. The plasma membrane may be the plasma membrane in a cell in which the construct/fusion protein has been expressed. In certain embodiments of the invention, a membrane-anchoring polypeptide domain may include a glycophosphatidylinositol (GPI) anchoring polypeptide, a one-pass transmembrane polypeptide, a channel complex-anchoring polypeptide, or a channel complex partner anchoring polypeptide.

A number of different GPI anchoring polypeptides are known in the art and may be used in a construct/fusion protein of the invention. Non-limiting examples of amino acid sequences that in certain embodiments of the invention may be added at the C-terminus of a construct/fusion protein. For example, a GPI anchoring polypeptide may include an amino acid sequence derived from a 5'-nucleotidase polypeptide, an acetylcholinesterase polypeptide, a CD48 polypeptide, a complement decay-accelerating factor polypeptide, or a lynx-1 polypeptide. In certain embodiments, a construct/fusion protein may include a membrane-anchoring polypeptide domain of a 5'-nucleotidase polypeptide. Non-limiting examples of GPI anchoring polypeptides include a *Homo sapiens* 5'-nucleotidase membrane-anchor polypeptide having the amino acid sequence RIKF-STGSHCHGSFSLIFLSLWAVIFVLYQ (SEQ ID NO:41), a Pacific electric ray acetylcholinesterase membrane-anchor polypeptide having the amino acid sequence GELSSSGTSSSKGIIFYVLFSILYLIF (SEQ ID NO:42), a *Rattus norvegicus* CD48 membrane-anchor polypeptide having the amino acid sequence LARSSGVHWI-AAWLVVTLSIIPSILLA (SEQ ID NO:43), a *Homo sapiens* Complement decay-accelerating factor membrane-anchor polypeptide having the amino acid sequence SGTTSGT-TRLLSGHTCFTLTGLLGTLVTMGLLT (SEQ ID NO:44), a *Mus musculus* lynx-1 membrane-anchor polypeptide having the amino acid sequence YLCNGAGFATPVTLA-LVPALLATFWSLL (SEQ ID NO:45), or a derivative thereof. In a particular embodiment, the amino acid sequence YLCNGAGFATPVTLALVPALLATFWSLL (SEQ ID NO:46, is added to the C-terminus of the construct/fusion protein so that the construct/fusion protein is GPI anchored to a membrane.

In certain embodiments, the construct/fusion protein includes a membrane-anchoring polypeptide domain that is a one-pass transmembrane polypeptide. Non-limiting examples of one-pass transmembrane polypeptides that may be used in constructs/fusion proteins and methods of the invention, include an amino acid sequence derived from an amino acid sequence of a platelet-derived-growth factor (PDGF) receptor polypeptide, a major histocompatibility Complex I polypeptide, a CD1b polypeptide, or a CD1c polypeptide. Non-limiting examples of one-pass transmembrane polypeptides include the *Homo sapiens* Beta Platelet-derived-growth factor receptor transmembrane-anchor polypeptide having the amino acid sequence RNAVGQDTQEVIVVPHSLPFKVVVISAILALVVLTIIS-LIILIMLWQKKPR (SEQ ID NO:47), artificial Beta Platelet-derived-growth factor receptor transmembrane-anchor polypeptide having the amino acid sequence RVA-VGQDTQEVIVVPHSLPFKVVVISAILALVVLTIISLIIL-IMLWQKKPRRIR (SEQ ID NO:48), a *Rattus norvegicus* Major Histocompatibility Complex I transmembrane-anchor polypeptide having the amino acid sequence QDPSTDSN-METTVIYVILGAVAMIGAVAIIGAMVAVVRRRKRN-TGGKGGDYAPAPGRDS SQSSDVSLPDCKA (SEQ ID NO:49), a *Homo sapiens* CD1b transmembrane-anchor polypeptide having the amino acid sequence QDII-LYWRNPTSIGSIVLAIIVPSLLLLLCLA-LWYMRRRSYQNIP (SEQ ID NO:50), a *Homo sapiens* CD1c transmembrane-anchor polypeptide having the amino acid sequence QDIILYWGHHFSMNWIALVVIVPLVIL-IVLVLWFKKHCSYQDIL (SEQ ID NO:51), or a derivative thereof.

Transmembrane domains such as one-pass transmembrane polypeptides disclosed herein can be added at the C-terminus of the other domains in a construct/fusion protein of the invention, which results in membrane localization of the construct/fusion protein. In certain embodiments of the invention a transmembrane domain may be used to express a construct/fusion protein at a cell location, examples of which include, but are not limited to, the cell surface (for example on the external or internal surface of the plasma membrane), the nuclear membrane, a mitochondrial membrane, an organelle membrane, etc.). A transmembrane domain sequence that is used in compositions and methods of the invention may further include a fluorescent protein marker. A protein marker (also referred to herein as a reporter molecule) may be used for tracking the position and location of a construct/fusion protein of the invention.

In certain embodiments, the construct/fusion protein includes a membrane-anchoring polypeptide domain that is a channel complex-anchoring polypeptide. A non-limiting example of a channel complex-anchoring polypeptide that may be used in constructs/fusion proteins and methods of the invention includes an amino acid sequence derived from a BKCA a polypeptide, e.g., a *Homo sapiens* BKCA alpha polypeptide set forth as KCMA1 HUMAN, Uniprot Q12791; an amino acid sequence derived from an amino acid sequence of a KChip1 polypeptide, e.g., a *Homo sapiens* KCIP1 polypeptide set forth as a KCIP1 HUMAN, Uniprot Q9NZI2.

It will be understood that membrane anchoring signal sequences disclosed herein are not intended to be limiting and that additional membrane anchoring polypeptides (and sequences thereof), etc. are well known in the art and may be included in a construct/fusion protein of the invention.

In certain aspects, the construct or a fusion protein harboring the same may include a reporter molecule. In certain embodiments, the reporter molecule is a reporter protein. In particular embodiments of the invention, a reporter protein is a fluorescent a reporter protein. In other embodiments, a reporter protein is an enzymatic reporter protein. Non-limiting examples of reporter proteins include, but are not limited to, mcherry, tdTomato, mPlum, Katushka, Neptune, green fluorescent protein (GFP), Yellow fluorescent protein (YFP), miniSOG, Luciferase, β-lactamase, etc. See, e.g., Shaner, et al. (2005) *Nat. Methods* 2:905-909; Shu, et al. (2011) *PLoS Biol.* 9:e1001041; and Qureshi (2007) *BioTechniques* 42:91. Inclusion and use of reporter molecules with fusion proteins is well-known in the art. Methods of including and/or encoding a reporter molecule, such as a reporter protein in a construct or fusion protein of the invention, and methods of monitoring and imaging such a reporter protein can be performed using routine methods known in the art.

Polynucleotides.

Certain aspects of the invention include methods for preparing and using polynucleotides encoding the construct of the invention, or a fusion protein comprising said construct (i.e., a protein of interest harboring a light-responsive construct). The invention, in part, also includes polynucleotides that encode constructs or fusion proteins of the invention as well as vectors and host cells that comprise such polynucleotides. Thus, in certain embodiments of the invention, a vector may be prepared that includes a polynucleotide that encodes a construct or fusion protein disclosed herein. In certain embodiments, the invention includes expression of a construct or fusion protein encoded by the polynucleotide in cells, tissues, or organisms. Also included in some aspects of the invention are methods of combinatorial optimization of a polynucleotide encoding a construct or fusion protein through targeted polypeptide site-directed mutagenesis, wavelength-specific photoreceptor sequences, etc. The construct or fusion protein of the invention may be genetically expressed in specific cells (e.g., using a virus or other vector) and then used to control cells in intact organisms (including humans) as well as in in vitro and ex vivo cells in response to pulses of light.

The present invention includes, in part, the expression and use of a novel class of constructs, to alter the function of proteins of interest in cells and membranes. In certain embodiments of the invention one or more fusion proteins may be expressed in cells that are in culture, in a subject, or isolated cells. Fusion proteins of the invention may include polypeptides comprising amino acid sequences derived from any organism. For example, a fusion protein of the invention may include a polypeptide derived from a human polypeptide, a rat polypeptide, a plant polypeptide, a mouse polypeptide, etc. It will be understood that each polypeptide in a single fusion protein need not be derived from the same organism. As used herein with respect to amino acid and nucleic acid sequences, the term "derived from" includes a sequence that is the same as a sequence identified in an organism and also includes a sequence that has been modified from a sequence identified in an organism. A polypeptide of the fusion protein having one or more substitutions or other modifications can be identified and tested for characteristics including, but not limited to: expression, cell localization, responses in dark and light conditions, etc.

A polypeptide of the fusion protein of the invention may include amino acid variants (e.g., polypeptides having a modified sequence) of the sequences as set forth herein. Modified sequences may have at least about 75%, 80%, 85%, 90%, 95%, 96%, 97%, 98%, 99%, or 100% identity with the polypeptide sequence of a polypeptide sequence disclosed herein. Identity in this context means sequence similarity. Such sequence identity can be determined using standard techniques known in the art. Fusion proteins of the present invention include the fusion protein sequences provided herein and variants that have more than about 50%, 55%, 60%, 65%, 70%, 75%, 80%, 85%, 90%, 95%, 96%, 97%, 98%, or 99% identity to a provided fusion protein.

Sequence modifications can be in one or more of three classes: substitutions, insertions or deletions. These modified sequences, (which may also be referred to herein as variants or derivatives) ordinarily are prepared by site specific mutagenesis of nucleic acids in the DNA encoding a fusion protein, using cassette or PCR mutagenesis or other techniques known in the art, to produce DNA encoding the modified fusion protein. Amino acid sequence variants are characterized by the predetermined nature of the variation, thus, a variant may be designed and selected based on knowledge of a fusion protein sequence of the invention. Modified fusion proteins may exhibit the same qualitative biological activity as the originating fusion protein from which they are derived or may be designed and selected to have one or more modified characteristics.

A site or region for introducing an amino acid sequence modification in a fusion protein may be predetermined, and the mutation per se need not be predetermined. For example, to optimize the performance of a mutation at a given site, random mutagenesis may be conducted at the target codon or region and the expressed modified fusion protein screened for the optimal combination of desired activity. Techniques for making substitution mutations at predetermined sites in DNA having a known sequence are well known, for example, M13 primer mutagenesis and PCR mutagenesis.

Substitutions, deletions, insertions or any combination thereof may be used to arrive at a one or more modified domains in a fusion protein of the invention. Generally, these changes are done on a few amino acids to minimize the alteration of the molecule. However, larger changes may be tolerated in certain circumstances.

Variants of fusion proteins set forth herein, may exhibit the same qualitative activity as one or more of the fusion protein sequences set forth herein, but may show some altered characteristics such as altered stability, speed, reversibility, compatibility, or toxicity, or a combination thereof. In addition, a fusion protein of the invention can incorporate unnatural amino acids as well as natural amino acids. An unnatural amino acid can be included in a fusion protein of the invention to enhance a characteristic such as altered photocurrent, stability, speed, reversibility, compatibility, or to lower toxicity, etc.

One skilled in the art will be able to identify additional polypeptide sequences that may be used in polypeptide domains of fusion proteins of the invention. For example, sequences with sufficient amino acid sequence homology to sequences provided herein, sequences modified from sequences provided herein, etc. A skilled artisan can also select one or more polypeptide sequences in addition to those disclosed herein that may be included in a fusion protein.

Another aspect of the invention provides polynucleotide sequences that code for a fusion protein of the invention. It would be understood by a person of skill in the art that the fusion protein of the present invention can be coded for by various nucleic acids. Each amino acid in the protein is represented by one or more sets of three nucleic acids (codons). Because many amino acids are represented by more than one codon, there is not a unique polynucleotide sequence that codes for a given protein. It is well understood by those of skill in the art how to make a polynucleotide that can code for a fusion protein of the invention by knowing the amino acid sequence of the protein. A polynucleotide sequence that codes for a polypeptide or protein is the "gene" of that polypeptide or protein. A gene can be RNA, DNA, or other nucleic acid than will code for the polypeptide or protein.

Delivery of the fusion protein to a cell and/or expression of a fusion protein in a cell can be done using art-known delivery means. In certain embodiments of the invention, the fusion protein may be delivered to a cell in the form of a polynucleotide that encodes the fusion protein. It is well known in the art how to prepare such polynucleotides and express the same in a cell of interest. Preferably, the fusion protein is non-toxic, or substantially non-toxic in cells in which it is expressed. Ideally, in the absence of light, a fusion protein of the invention may not significantly alter cell health or ongoing cellular activity in the cell in which it is expressed. However, in the presence of light, a fusion protein of the invention may alter cell health or ongoing cellular activity in the cell in which it is expressed.

Certain aspects of the invention include a vector for expressing a fusion protein in a cell. As used herein, the term "vector" refers to a nucleic acid molecule capable of transporting between different genetic environments another nucleic acid (e.g., polynucleotide) to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert a polynucleotide encoding a fusion protein into dividing and non-dividing cells that are either in vivo, in vitro, or ex vivo cells. Vectors useful in methods of the invention may include additional sequences including, but not limited to one or more signal sequences and/or promoter sequences, or a combination thereof. Expression vectors and methods of their use are well known in the art.

In certain embodiments of the invention, a vector may be a lentivirus harboring the gene for a fusion protein of the invention, or a variant thereof. A lentivirus is a non-limiting example of a vector that may be used to create a stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general-purpose promoter that allows expression of a fusion protein in a wide variety of cell types is, for example, a "housekeeping gene." Non-limiting examples of general promoters are provided elsewhere herein and suitable alternative promoters are well known in the art. In certain embodiments of the invention, a promoter may be an inducible promoter, examples of which include, but are not limited to, tetracycline-on or tetracycline-off, or tamoxifen-inducible Cre-ER, etc.

Methods of Making and Using a Fusion Protein.

In some aspects of the invention, methods of preparing a fusion protein of the invention are provided. Such methods, which are also referred to herein as methods of manufacturing, may include delivering to a cell a polynucleotide that encodes the fusion protein of the invention; and expressing in the cell the fusion protein encoded by the polynucleotide. Methods of making the fusion protein of the invention may also include expressing the fusion protein in an isolated cell, a cell in culture, a cell in a subject, a cell in solution, etc. A cell may be an in vivo cell, an in vitro cell, or an ex vivo cell. Non-limiting examples of cell types in which a fusion protein of the invention can be prepared are neuronal cells, cardiac cells, lymphocytes, leukocytes, glial cells, neuroglial cells, macroglial cells, astrocytes, oligodendrocytes, Schwann cells, and microglial cells. A cell in which a fusion protein of the invention is expressed, may in certain embodiments be an immortal cell or a tumor cell.

In certain embodiments of the invention, the fusion protein or the polynucleotide that encodes the fusion protein may be delivered to the cell by means of a pharmaceutical composition which includes the fusion protein or the polynucleotide in admixture with a pharmaceutically acceptable excipient. Thus, in one aspect, a pharmaceutical composition that includes the polynucleotide can be prepared and delivered to a cell and the fusion protein expressed in the cell.

In certain embodiments, the invention also includes a method of regulating an activity of a protein of interest. The method includes inserting into a domain (e.g., catalytic domain or activation loop) of the protein of interest a light-responsive construct of this invention thereby creating a fusion protein and exposing the fusion protein to an effective dose of a light to modulate a conformation of the fusion protein, wherein the modulation of the conformation of the fusion protein regulates the activity of the fusion protein. In some embodiments, the method is carried out in a cell. Accordingly, the invention also provides a method for modulating the conformation and/or activity of a protein of interest in a cell by delivering to a cell a polynucleotide that encodes a fusion protein (i.e., a protein of interest harboring a light-responsive construct of the invention); expressing in the cell the fusion protein encoded by the polynucleotide; and contacting the expressed fusion protein with an effective dose of a light to modulate a conformation of the fusion protein, wherein the modulation of the conformation of the fusion protein alters a functional state of the fusion protein. In certain embodiments of the method, the cell is in vitro. In other embodiments, the cell is in a subject. In particular embodiments, the subject may have been diagnosed with, or expected to have, a neurological, cancer, immune system, or cardiac disease or condition.

In certain embodiments, the invention also includes methods of determining the effect of a candidate therapeutic compound on a functional state of a protein of interest. As used herein the term "determining" in the context of the method may include measuring or assessing whether or not there is an effect. The methods of determining the effect of a candidate therapeutic compound may include delivering to a cell a polynucleotide that encodes a fusion protein (i.e., an enzyme having inserted in its catalytic domain a light-responsive construct of the invention); expressing in the cell the fusion protein encoded by the polynucleotide; contacting the cell with a candidate therapeutic compound; contacting the expressed fusion protein with a dose of a light effective to modulate a conformation of the fusion protein; determining the determined functional state of the fusion protein; and comparing the determined functional state of the fusion protein with a control functional state of the fusion protein, wherein a difference between the determined functional state and the control functional state indicates an effect of the candidate therapeutic compound on the fusion protein.

A cell used in methods and with the compositions of the invention may be a prokaryotic or a eukaryotic cell. Useful cells include but are not limited to mammalian cells. Examples of cell types that may be used in methods of the invention include, but are not limited to neuronal cells, muscle cells, cardiac cells, secretory cells (such as pancreatic cells, adrenal medulla cells, pituitary cells, etc.), lymphocytes, leukocytes; glial cells, neuroglial cells, macroglial cells, astrocyte cells, oligodendrocyte cells, Schwann cells, and microglial cells. In certain embodiments of the invention, a cell may be an immortal cell or may be a tumor cell.

In certain embodiments, a cell used in conjunction with the invention may be a healthy normal cell, which is not known to have a disease, disorder or abnormal condition. In certain embodiments, a cell used in conjunction with methods and fusion proteins of the invention may be an abnormal cell, for example, a cell that has been diagnosed as having a disorder, disease, or condition including, but not limited to, a cancer or a neurological or cardiac disease or condition such as epilepsy, drug-resistant depression, schizophrenia, tachycardia, bradycardia, atrial fibrillation, LongQT syndrome, glioblastoma, medullablastoma, neuroblastoma, leukemia, or lymphoma, an injured cell, etc. In certain embodiments of the invention, a cell may be a control cell.

Fusion proteins of the invention may be expressed in cells from culture, cells in solution, cells obtained from subjects, and/or cells in a subject (in vivo cells), ex vivo cells, in vitro cells, etc. Fusion proteins may be expressed and activated in cultured cells, cultured tissues (e.g., brain slice preparations, etc.), and in living subjects, etc. As used herein, the term "subject" may refer to a human, non-human primate, cow, horse, pig, sheep, goat, dog, cat, rodent, bird, reptile, insect, fish, fly or any other vertebrate or invertebrate organism.

Fusion proteins of the invention and methods using fusion proteins of the invention can be used to assess changes in cells, tissues, and subjects in which they are expressed. Certain embodiments of the invention include use of fusion proteins of the invention to identify effects of candidate compounds on cells, tissues, and subjects. Results of testing fusion proteins of the invention can be advantageously compared to a control.

As used herein a control may be a predetermined value, which can take a variety of forms. It can be a single cut-off value, such as a median or mean. It can be established based upon comparative groups, such as cells or tissues that include the fusion protein and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

In certain embodiments, fusion proteins of the invention can be used in test systems and assays for assessing effects of candidate therapeutic agents, effect of expression of modified kinases, phosphatases or recombinases, etc. Fusion proteins of the invention can be used to test compounds to treat diseases or conditions such as cancer or a neurological disease or condition or a cardiac disease or condition.

Some aspects of the invention include a light responsive treatment method using one or more fusion proteins of the invention. Treatment methods of the invention may include administering to a cell, tissue or subject in need of such treatment, a therapeutically effective amount of a fusion protein of the invention to treat a disease, condition or disorder and activating the fusion protein by exposing the cell, tissue or subject to light. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need not entirely eliminate the disease, disorder, or condition to be effective.

Administration of a fusion protein of the invention may include administration of a pharmaceutical composition that includes a cell, wherein the cell expresses the fusion protein. Administration of a fusion protein of the invention may include administration of a pharmaceutical composition that includes a vector, wherein the vector comprises a polynucleotide encoding the fusion protein and the administration of the vector results in expression of the fusion protein in one or more cells in the subject.

An effective amount of a fusion protein is an amount that increases the level of the fusion protein in a cell, tissue or subject to a level that is beneficial for the subject. An effective amount may also be determined by assessing physiological effects of administration on a cell or subject, such as a decrease in symptoms following administration. Other assays will be known to one of ordinary skill in the art and can be employed for measuring the level of the response to a treatment. The amount of a treatment may be varied for example by increasing or decreasing the amount of the fusion protein administered, by changing the therapeutic composition in which the fusion protein is administered, by changing the route of administration, by changing the dosage timing and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the fusion protein is to be expressed. An effective amount may also depend on the location of the tissue to be treated.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of a composition to increase the level of a fusion protein (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A fusion protein of the invention may be administered using art-known methods. The manner and dosage administered may be adjusted by the individual physician or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver fusion proteins of the invention may be administered alone, in combination with each other, and/or in combination with other drug therapies, or other treatment regimens that are administered to subjects. The dose of a pharmaceutical composition that is administered to a subject to increase the level of fusion protein in cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of the fusion protein of the invention (e.g., light wavelength, length of light contact, etc.) that has been administered to a subject can also be adjusted based on efficacy of the treatment in a particular subject. Parameters for illumination and activation of fusion proteins (or enzyme of interest containing the same) that have been administered to a subject can be determined using art-known methods and without requiring undue experimentation.

Various modes of administration will be known to one of ordinary skill in the art that can be used to effectively deliver a pharmaceutical composition to increase the level of fusion protein (or enzyme of interest containing the same) in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of a therapeutic compound will be known to one of ordinary skill in the art, in which the dose amount, schedule of administration, sites of administration, mode of administration (e.g., intra-organ) and the like vary from those presented herein.

Administration of a cell or vector to increase a fusion protein level in a mammal other than a human; and administration and use of fusion proteins of the invention, e.g. for testing purposes or veterinary therapeutic purposes, may be carried out under substantially the same conditions as described above. It will be understood by one of ordinary skill in the art that this invention is applicable to both human and animals. Thus, this invention is intended to be used in husbandry and veterinary medicine as well as in human therapeutics.

In some aspects of the invention, methods of treatment using a fusion protein of the invention are applied to cells including but not limited to a nervous system cell, a neuron, a cardiovascular system cell, a circulatory system cell, a visual system cell, an auditory system cell, a muscle cell, an endocrine cell, a secretor cell (such as pancreatic cells, adrenal medulla cells, pituitary cells, etc.), an immune system cells, (e.g., lymphocytes, leukocytes, etc.). Examples of nervous system cells to which a treatment of the invention can be applied include, but are not limited to: glial cells, neuroglial cells, macroglial cells, astrocyte cells, oligodendrocyte cells, Schwann cells, and microglial cells.

Disorders and conditions that may be treated using methods of the invention include, cancer, injury, brain damage, degenerative neurological conditions, cardiovascular conditions, and may include treatment of diseases and conditions such as neurological or cardiac disease including, but not limited to Epilepsy, drug-resistant depression, schizophrenia, tachycardia, bradycardia, atrial fibrillation, LongQT syndrome, glioblastoma, medullablastoma, neuroblastoma, leukemia, lymphoma, etc.

The following non-limiting examples are provided to further illustrate the present invention.

Example 1: Optogenetic Regulation of Protein Kinases

A wide array of oncogenic processes is controlled by kinase-mediated phosphorylation. Kinases represent the second largest class of enzymes selected as targets for antitumor therapy. The role of different kinases in regulation of oncogenic transformation, tumor progression and metastasis has been a subject of extensive studies. An established paradigm in kinase-mediated signal transduction is the critical influence of the timing and the location of kinase activation on signaling output and biological response. However, the extent to which kinase signaling depends on its tight temporal and spatial regulation is unknown, largely due to the paucity of tools that allow kinases to be controlled in space and time. Temporal control over kinase activation may be especially important for understanding the role of oscillation of kinase activity in regulation of physiologic and pathophysiologic cell signaling. Cyclin dependent kinases which drive cell proliferation in cancer cells, for example, are known to oscillate in their activity levels. However, the temporal nature of signaling by other oncogenic kinases is much less understood.

Constitutive activation of a kinase in cancer cells is only present for a subset of oncogenic kinases that are mutationally activated. For many oncogenic signaling pathways, mutations occur upstream of kinases and the kinases themselves likely exhibit cyclical or oscillatory activation. Current tools for regulation of kinases are limited in their ability to mimic this oscillating activity of kinases in living cells.

The innovative fusion protein described herein can be summarized as follows:

Light-mediated allosteric regulation of kinase activity provides for reversible regulation of kinase activity by light with precise temporal control. The catalytic domain of kinases is regulated specifically without affecting scaffolding or other functions of the enzyme. Regulation of activity is achieved only by illumination with blue light, which minimizes side effects and simplifies manipulation of signaling. The novel compositions and methods described herein confer tight temporal control of kinase activation and inactivation. This approach enables regulation of a kinase far faster than genetic manipulation and enables manipulation of highly dynamic cellular processes.

Unlike traditional pharmacological agents, the fusion protein described herein act only on the kinase containing the fusion protein insertion. This will enable selective manipulation of one kinase even within a closely homologous family.

The disclosed method for optogenetic regulation of kinases enables localized control of kinase activity in specific subcellular locations.

Using the fusion protein and methods described herein, any kinase or enzyme can be regulated by light, thereby providing broad applicability to dissect biological processes and signaling pathways.

Example 2: Optogenetic Regulation of Src

Tyrosine kinase Src is a known oncoprotein, the signaling of which is tightly controlled in space and time during physiological function and often dysregulated in many cancers. Development of light-regulated Src will allow for control of its activity locally and temporally. This will provide new opportunities for interrogation of Src's signaling involved in tumorigenesis. The structure of the catalytic domains for most protein kinases is highly conserved (Krupa, et al. (2004) *J. Mol. Biol.* 339:1025-1039; Scheeff & Bourne (2005) *PLoS Comput. Biol.* 1:e49). Thus, the demonstrated regulation of Src will be applicable for regulation of other kinases.

To design an allosteric switch for regulation of kinases, a light sensitive LOV domain from *Neurospora crassa* VVD protein (VVD) was selected. Each VVD domain was composed of residues His37 to Glu184 of *Neurospora crassa* VIVID, which was identified as the minimal fragment of VVD required for efficient dimerization and light-mediated regulation. The minimal VVD domains were fused in frame and separated by a long linker composed Gly-Ser-Gly repeats. The resulting construct is set forth herein in SEQ ID NO:52). Upon illumination with blue light (below 500 nm wavelength), VVD dimerizes. Structural analysis of VVD reveals that light-induced dimerization is also accompanied by a conformational change that positions the N-terminus of one VVD domain close to the C-terminus of the other VVD domain in the dimer. In the dark, the N-terminal residues of VVD are oriented in the opposite direction. By connecting two VVD domains into one protein an engineered fusion protein or "clamp" (LightR-clamp) is generated that dramatically changes orientation of its N- and C-termini upon illumination with blue light. In the dark, VVD domains do not dimerize and the N-terminus of the LightR-clamp is positioned away from the C-terminus. Illumination with light causes VVD dimerization and reorientation of the N-terminus so it is positioned next to the C-terminus (FIG. 2). Insertion of this fusion protein into the catalytic domain of a kinase allows for local structural changes in the kinase upon exposure to light thereby providing for allosteric control of kinase activity.

It has been shown that insertion of an allosteric switch at position Gly288 in the catalytic domain of c-Src enables regulation of its activity (Karginov, et al. (2010) *Nat. Biotechnol.* 28:743-747; Karginov, et al. (2014) *Nat. Chem. Biol.* 10:286-290). Gly288 is directly connected to a conserved structural element, the G-loop that is critical for phosphate transfer catalysis. Accordingly, the LightR-claim construct was inserted into c-Src at position Gly288 and the resulting fusion protein is set forth herein as SEQ ID NO:53. Insertion of the LightR-clamp at the position Gly288 causes inactivating distortion in the Src catalytic domain because N- and C-termini of the clamp are far apart (FIG. 2). Illumination with light bring N- and C-termini of the LightR-clamp together and, thus, restores Src kinase activity. Importantly, Gly288 is positioned on the opposite side of the catalytic domain away from the catalytic pocket. This will ensure that LightR-clamp will not sterically block access to the substrates. For initial development, a Tyr529Phe mutant of Src was used to prevent regulation by endogenous factors and, thus, enable full control of Src activity only through the light-sensitive switch.

All initial experiments were performed in HEK293 cells. The results of this analysis indicated that illumination of cells expressing engineered Src with blue light stimulates phosphorylation of known Src substrates in reversible manner. These results demonstrate feasibility of using the LightR-clamp to regulation Src activity as well as other similar kinases.

Figure 3:
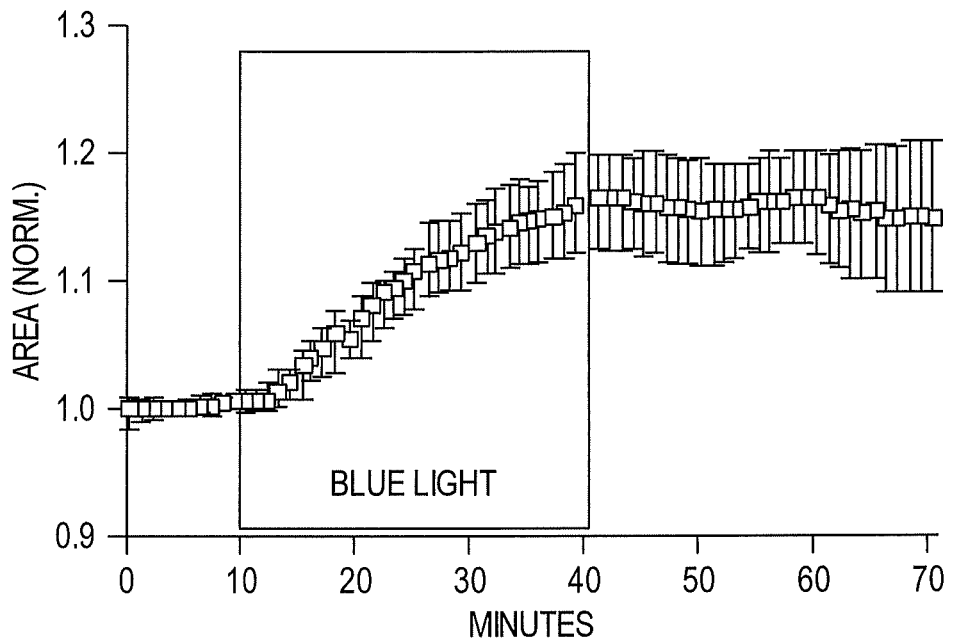
FIG. 3 shows light-mediated regulation of cell area using a LightR-Src fusion protein in HeLa cells.

Previous studies have shown that activation of endogenous c-Src induces its translocation from cytoplasmic/perinuclear area to plasma membrane and cell periphery (Sandilands, et al. (2007) J. Cell Sci. 120:2555-2564; Chu, et al. (2014) Proc. Natl. Acad. Sci. USA 111:12420-12425). Using the LightR-Src construct, similar translocation of LightR-Src upon activation with light was observed. Furthermore, LightR-Src stimulated cell spreading, a known Src-mediated morphological change (Karginov, et al. (2014) Nat. Chem. Biol. 10:286-290; Klomp, et al. (2016) Proc. Natl. Acad. Sci. USA 113:14976-81; Chu, et al. (2014) Proc. Natl. Acad. Sci. USA 111:12420-25). Importantly, spreading stopped when illumination of the cells was stopped thereby demonstrating reversible regulation of the kinase (FIG. 3).

Figure 4:
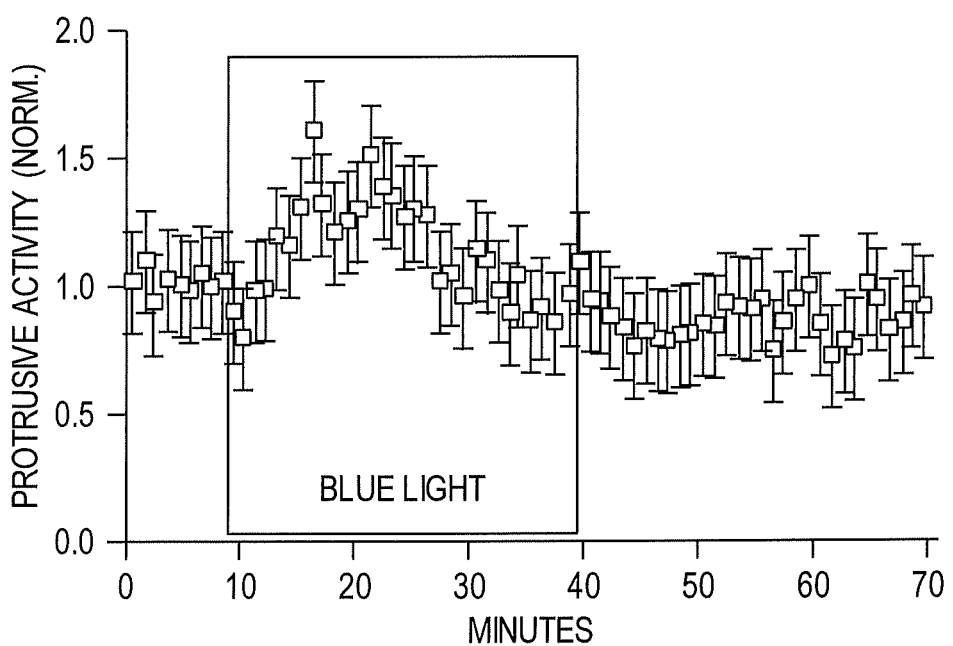
FIG. 4 shows light-mediated regulation of protrusive activity using a LightR-Src fusion protein in HeLa cells.
Figure 5:
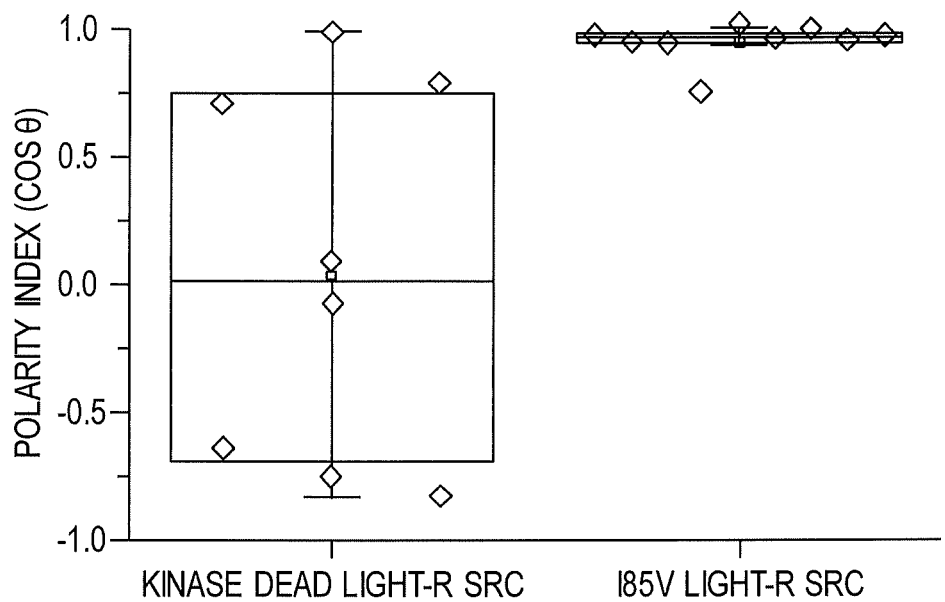
FIG. 5 shows light-mediated regulation of cell polarization using a LightR-Src fusion protein in HeLa cells.

Activation of Src is known to induce membrane protrusions and cells spreading (Karginov, et al. (2014) Nat. Chem. Biol. 10:286-290). Therefore, it was determined whether localized activation of Src would stimulate local protrusions and polarized cell spreading. To test this, a region of HeLa cells, which express LightR-Src, was illuminated and morphological changes were assess using live cell imaging according to established methods (Karginov, et al. (2014) Nat. Chem. Biol. 10:286-290; Klomp, et al. (2016) Proc. Natl. Acad. Sci. USA 113:149768-14981). The results of this analysis indicated that LightR-Src activation could induce temporary spreading (FIG. 4) and cell polarization, wherein no such cell polarization was observed when the LightR construct was inserted into a kinase inactive mutant of Src (D388R) (FIG. 5).

Figure 6:
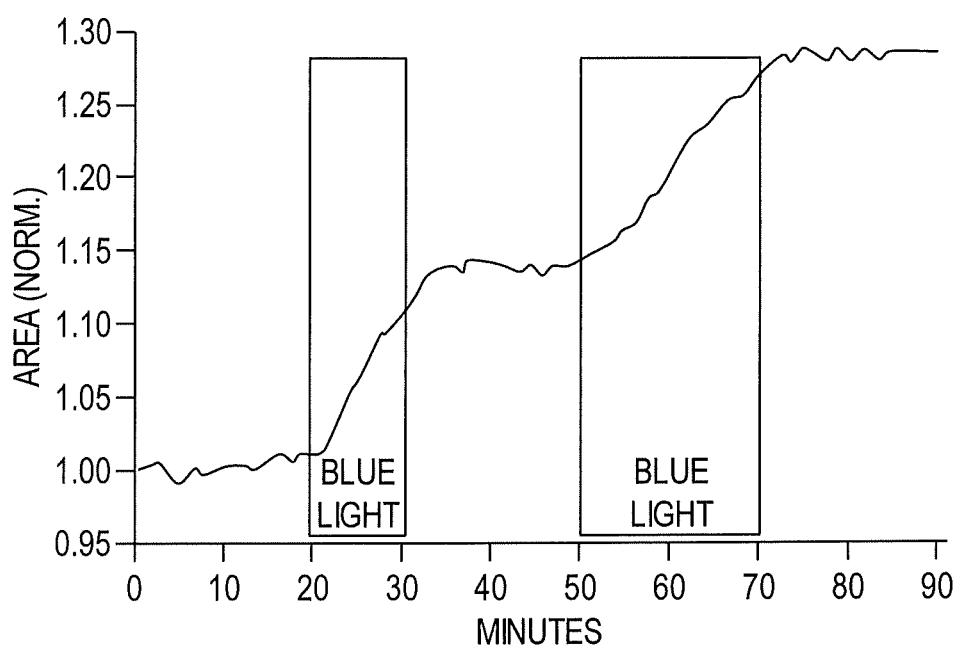
FIG. 6 shows that cell area could be repeatedly modulated by multiple rounds of activation and deactivation using LightR-Src.
Figure 7:
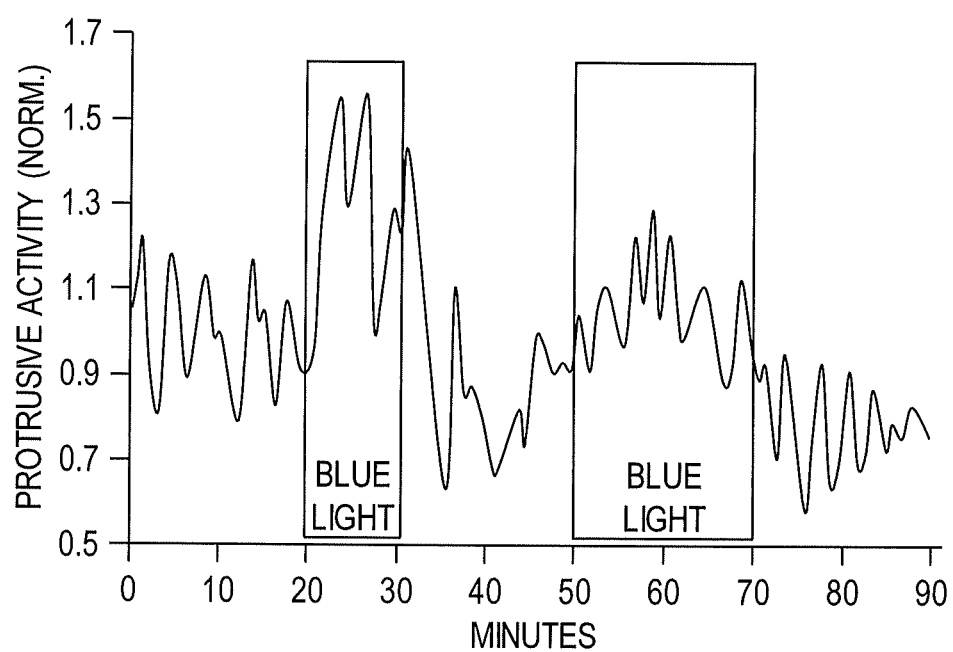
FIG. 7 shows that protrusive activity could be repeatedly modulated by multiple rounds of activation and deactivation using LightR-Src.

It was further determined whether changes in cell area and protrusive activity could be observed over multiple rounds of activation and deactivation using LightR-Src. This analysis demonstrated that spreading (FIG. 6) and protrusive activity (FIG. 7) could be repeatedly initiated and stopped using the LightR-Src construct.

The catalytic domains for protein kinases share high similarity (Krupa, et al. (2004) J. Mol. Biol. 339:1025-39; Scheef & Bourne (2005) PLoS Comput. Biol. 1:e49). Thus, like Src, other protein kinases can also be regulated by insertion of LightR-clamp domain at the same structural position as for Src, i.e., the Gly-rich loop. For example, structural analysis of cAb1 and PKA kinases indicates that Glu64 in PKA and Lys282 in cAb1 correspond to the Gly288 position where LightR-clamp was inserted in Src. Likewise, this corresponding position is well-known in other kinases (Table 1).

| Kinase Name | PDB ID | Structural Position corresponding to Gly288 of Src |
|---|---|---|
| ChaK | 1ia9 | Trp1633 |
| PI3K | 1e8x | Cys676 |
| CKA-2 | 1nw1 | Glu96 |
| PKA | 1cdk | Lys282 |
| PKB | 1o61 | Ala171 |
| GRK2 | 1omw | Asp212 |
| PDK1 | 1h1w | Ala103 |
| Aur2 | 1muo | Gln154 |

Location is with reference to sequence provided in PDB accession number. Adapted from FIG. 3 of Scheef & Bourne (2005) PLoS Comput. Biol. 1: e49.

Therefore, it is expected that insertion of LightR-clamp at these positions of the kinases disclosed herein will render them responsive to light activation. In particular, expression of recombinant Abl and PKA kinases in HEK293 cells will allow for light-activated regulation of phosphorylation of known endogenous substrates: caspase (Tyr153), Crk (Tyr221), Dok1 (Tyr361) and PKD (Tyr463) for cAb1 (Raina, et al. (2005) J. Biol. Chem. 280:11147-51; Feller, et al. (1994) EMBO J. 13:2341-51; Woodring, et al. (2004) J. Cell Biol. 165:493-503; Storz, et al. (2003) J. Biol. Chem. 278:17969-76); CREB (Ser133), GRK1 (Ser21), and NF-kappaB p65 subunit (Ser276) for PKA (Fiol, et al. (1987) J. Biol. Chem. 262:14042-48; Horner, et al. (2005) J. Biol. Chem. 280:28241-50; Zhong, et al. (1997) Cell 89:413-424).

The compositions and methods described herein will enable unprecedented control of key kinases involved in cancer signaling. The invention will provide specificity, tight temporal control of activation and inactivation, and ability to manipulate kinase signaling at specific locations within living cells. None of the existing methods for dissection of kinase function provide this combination of precision and broad applicability. Furthermore, the invention will establish guidelines for light-mediated allosteric regulation of other enzymes involved in oncogenic transformation. This method will allow for the identification of direct downstream targets of kinase activation in malignant cells leading to a profound increase in understanding fundamental aspects of cancer signaling and the development of novel therapies.

Example 3: Optogenetic Regulation of a Phosphatase

Src Homology 2 domain-containing phosphotyrosine phosphatase 2 (Shp2) is a ubiquitously expressed protein tyrosine phosphatase. Aberrant Shp2 signaling is associated with several pathologies; however, the exact role of Shp2 in various signaling pathways is less well defined. Current tools to study Shp2, such as expression of constitutively active or dominant negative Shp2 or small molecule inhibitors, evaluate the effect of long-term activation or depletion of Shp2. However, these studies often come to conflicting conclusions. To provide highly specific temporal and spatial regulation of Shp2 signaling, the LightR-clamp construct was inserted into the catalytic domain of Shp2 at Val406 to result in the a LightR-Shp2 fusion protein. Two fusion proteins with different off-kinetics (i.e., a dominant negative Shp2 and constitutively active Shp2) were tested in live HEK293 cells. Upon stimulation with blue light, VVD dimerizes and Shp2 catalytic activity is restored. LightR-Shp2 has the added advantage of deactivation; allowing for the investigation of transient Shp2 signaling and identification of secondary signaling events. Using this fusion protein, it was shown that LightR activates the MAPK pathway leading to ERK activation and dephosphorylate EGFR, PLCγ, and FAK in living cells. To further understand the effect of the insertion on catalytic activity, molecular dynamics simulations were performed to probe the conformational dynamics of LightR-Shp2 in the dark and light state. Furthermore, the effect of varied length of the amino acid sequence linking the light regulated domain to the catalytic domain of Shp2 was assessed. This analysis revealed a destabilization of the substrate binding domain and disruption of the WPD loop in the dark state. Continued disruption of the catalytic domain in the light state of a construct containing a sub-optimal linker length was also observed, in silico.

These data demonstrate that allosterically regulated tools can be used to probe physiologically relevant pathways to elucidate the various roles of protein phosphatases as well as providing insight into the design of other regulated enzymes. The catalytic domains for protein phosphatases share structurally conserved PTP domains (Andersen, et al. (2001) *Mol. Cell. Biol.* 21(21):7117-7136). Thus, like Shp2, other protein phosphatases can also be regulated by insertion of LightR-clamp domain at the same structural position as for Shp2. Such locations are known to be conserved amongst protein phosphatases. For example, structural analysis of more than protein phosphatases indicates that residues PXXVHCSAGXGRTG (SEQ ID NO:54; i.e., residues 210-223 of PTP1B) of the PTP loop are highly conserved residues, which surround the active site Cys. In addition, residues KXXKNRY (SEQ ID NO:55; i.e., residues 40-46 of PTP1B) of the pTyr-recognition loop are highly conserved residues that restrict substrate specificity to pTyr. See, Andersen, et al. (2001) *Mol. Cell. Biol.* 21(21):7117-7136. Moreover, Zhang & Bishop ((2007) *J. Am. Chem. Soc.* 129(13):3812-3813) teach locations within the catalytic domain of T-cell PTP (TCPTP), TPT1B and SHP1 that are permissible for amino acid insertions (e.g., residues 65, 78-80, 187-188, 208-209 and 241 of TCPTP). However, in certain embodiments, insertion of the light-responsive construct is in the β10 sheet of the phosphatase. It is expected that insertion of LightR-clamp at these positions of the phosphatases disclosed herein will render them responsive to light activation.

Example 4: Optogenetic Regulation of a Recombinases

In vivo lineage tracing has been revolutionized by the Cre/loxP system, whereby tissue-specific promoter activation of the Cre-recombinase leads to permanent activation of a reporter gene in a cell and all its downstream progeny. Fusion of the Cre enzyme to the estrogen receptor (ER), which prevents nuclear localization of the Cre-ER protein unless bound by an estrogen analog (e.g., tamoxifen), allows an additional level of temporal control of reporter activation. Tamoxifen (TAM) and its active metabolite form 4-hydroxytamoxifen (4-OHT) have brief half-lives upon injection into mice, thus restricting reporter induction to a 24- to 48-hour window when tamoxifen is active. Despite the utility of this system, tamoxifen diffuses rapidly in vivo, preventing precise spatial activation of a specific location or region within an organism.

Accordingly, this invention also provides for use of the light-responsive construct of the invention to regulate Cre recombination, e.g., in generating transgenic animals such as mice including the Cre/loxP system. The Cre/LoxP system is known in the art and is used to generate mice with conditional expression of genes of interest. Current methods for regulating Cre recombination include using cell-specific promoters or inducible promoters, e.g., Tet-regulatable system, to regulate expression of the Cre recombinase. In accordance with this invention, the light-responsive construct is insert, e.g., between amino acid residues 59 and 60 of Cre to generate a fusion protein of the invention. Insertion at this location has been shown to result in the lowest background with reasonably good activation. See, e.g., Jullien, et al. (2007) *PLoS One* 2(12):e1355).

What is claimed is:

1. A method of reversibly and allosterically regulating the activity of a non-receptor tyrosine kinase comprising:
    inserting into the glycine-rich loop of the catalytic domain of the non-receptor tyrosine kinase a light-responsive construct comprising a first photoreceptive polypeptide domain and a second photoreceptive polypeptide domain, wherein said first and second photoreceptive polypeptide domains are the same and:
    (i) are operatively-linked via a flexible linker;
    (ii) comprise
        (a) amino acid residues 37-184 of SEQ ID NO:1,
        (b) amino acid residues 40-186 of SEQ ID NO:1,
        (c) a variant of (a) or (b) comprising one or more amino acid substitutions selected from the group consisting of Ile74Val, Ile85Val, Met135Ile, and Met165Ile, or
        (d) a variant of amino acids 37-186 of SEQ ID NO:1 comprising one or more amino acid substitutions selected from the group consisting of Ile74Val, Ile85Val, Met135Ile, and Met165Ile; and
    (iii) homodimerize with each other thereby producing a fusion protein; and
    exposing the fusion protein to an effective dose of a light to modulate a conformation of the fusion protein, wherein the modulation of the conformation of the fusion protein regulates the activity of the non-receptor tyrosine kinase.

2. The method of claim 1, wherein the flexible linker comprises 20 to 100 amino acid residues.

3. The method of claim 1, wherein the flexible linker comprises one or more Gly-Ser-Gly motifs.

4. The method of claim 1, wherein the non-receptor tyrosine kinase is SRC, FGR, FYN, YES1, BLK, HCK, LCK, LYN, ABL1, ARG, ACK1, TNK1, CSK, MATK, FAK, PYK2, FES, FER, FRK, BRK, SRMS, JAK1, JAK2, JAK3, TYK2, TEC, BMX, BTK, ITK, TXK, SYK or ZAP10.

5. The method of claim 4, wherein the activity of the kinase is phosphorylation.

6. A fusion protein comprising a non-receptor tyrosine kinase having inserted in the glycine-rich loop of the catalytic domain of the non-receptor tyrosine kinase a light-responsive construct comprising a first photoreceptive polypeptide domain and a second photoreceptive polypeptide domain, wherein said first and second photoreceptive polypeptide domains are the same:
    (i) are operatively-linked via a flexible linker;
    (ii) comprise
        (a) amino acid residues 37-184 of SEQ ID NO:1,
        (b) amino acid residues 40-186 of SEQ ID NO:1,
        (c) a variant of (a) or (b) comprising one or more amino acid substitutions selected from the group consisting of Ile74Val, Ile85Val, Met135Ile, and Met165Ile, or
        (d) a variant of amino acids 37-186 of SEQ ID NO:1 comprising one or more amino acid substitutions selected from the group consisting of Ile74Val, Ile85Val, Met135Ile, and Met165Ile; and
    (iii) homodimerize with each other.

7. The fusion protein of claim 6, wherein the non-receptor tyrosine kinase is SRC, FGR, FYN, YES1, BLK, HCK, LCK, LYN, ABL1, ARG, ACK1, TNK1, CSK, MATK, FAK, PYK2, FES, FER, FRK, BRK, SRMS, JAK1, JAK2, JAK3, TYK2, TEC, BMX, BTK, ITK, TXK, SYK or ZAP10.

8. The method of claim 1, wherein the non-receptor tyrosine kinase is mammalian.

9. The fusion protein of claim 6, wherein the non-receptor tyrosine kinase is mammalian.

10. The method of claim 1, wherein said first and second photoreceptive polypeptide domains consist of:
    (a) amino acid residues 37-184 of SEQ ID NO:1,
    (b) amino acid residues 40-186 of SEQ ID NO:1,
    (c) a variant of (a) or (b) consisting one or more amino acid substitutions selected from the group consisting of Ile74Val, Ile85Val, Met135Ile, and Met165Ile, or
    (d) a variant of amino acids 37-186 of SEQ ID NO:1 consisting one or more amino acid substitutions selected from the group consisting of Ile74Val, Ile85Val, Met135Ile, and Met165Ile.

11. The fusion protein of claim 6, wherein said first and second photoreceptive polypeptide domains consist of:
    (a) amino acid residues 37-184 of SEQ ID NO:1,
    (b) amino acid residues 40-186 of SEQ ID NO:1,
    (c) a variant of (a) or (b) consisting one or more amino acid substitutions selected from the group consisting of Ile74Val, Ile85Val, Met135Ile, and Met165Ile, or
    (d) a variant of amino acids 37-186 of SEQ ID NO:1 consisting one or more amino acid substitutions selected from the group consisting of Ile74Val, Ile85Val, Met135Ile, and Met165Ile.

12. A method of reversibly and allosterically regulating the activity of a non-receptor tyrosine kinase comprising:
    inserting into the glycine-rich loop of the catalytic domain of the non-receptor tyrosine kinase a light-responsive construct comprising a first photoreceptive polypeptide domain and a second photoreceptive polypeptide domain, wherein said first and second photoreceptive polypeptide domains:
    (i) are operatively-linked via a flexible linker;
    (ii) independently comprise
        (a) amino acid residues 37-184 of SEQ ID NO:1,
        (b) amino acid residues 40-186 of SEQ ID NO:1,
        (c) a variant of (a) or (b) comprising one or more amino acid substitutions selected from the group consisting of Ile74Val, Ile85Val, Met135Ile, and Met165Ile, or
        (d) a variant of amino acids 37-186 of SEQ ID NO:1 comprising one or more amino acid substitutions selected from the group consisting of Ile74Val, Ile85Val, Met135Ile, and Met165Ile; and
    (iii) are capable of dimerizing with each other thereby producing a fusion protein; and
    exposing the fusion protein to an effective dose of a light to modulate a conformation of the fusion protein, wherein the modulation of the conformation of the fusion protein regulates the activity of the non-receptor tyrosine kinase.

13. The method of claim 12, wherein the flexible linker comprises 20 to about 100 amino acid residues.

14. The method of claim 12, wherein the flexible linker comprises one or more Gly-Ser-Gly motifs.

15. The method of claim 12, wherein the non-receptor tyrosine kinase is SRC, FGR, FYN, YES1, BLK, HCK, LCK, LYN, ABL1, ARG, ACK1, TNK1, CSK, MATK, FAK, PYK2, FES, FER, FRK, BRK, SRMS, JAK1, JAK2, JAK3, TYK2, TEC, BMX, BTK, ITK, TXK, SYK or ZAP10.

16. The method of claim 12, wherein the activity of the kinase is phosphorylation.

17. A fusion protein comprising a non-receptor tyrosine kinase having inserted in the glycine-rich loop of the catalytic domain of the non-receptor tyrosine kinase a light-responsive construct comprising a first photoreceptive polypeptide domain and a second photoreceptive polypeptide domain, wherein said first and second photoreceptive polypeptide domains:
  (i) are operatively-linked via a flexible linker;
  (ii) independently comprise
    (a) amino acid residues 37-184 of SEQ ID NO:1,
    (b) amino acid residues 40-186 of SEQ ID NO:1,
    (c) a variant of (a) or (b) comprising one or more amino acid substitutions selected from the group consisting of Ile74Val, Ile85Val, Met135Ile, and Met165Ile, or
    (d) a variant of amino acids 37-186 of SEQ ID NO:1 comprising one or more amino acid substitutions selected from the group consisting of Ile74Val, Ile85Val, Met135Ile, and Met165Ile; and
  (iii) are capable of dimerizing with each other.

18. The fusion protein of claim 17, wherein the non-receptor tyrosine kinase is SRC, FGR, FYN, YES1, BLK, HCK, LCK, LYN, ABL1, ARG, ACK1, TNK1, CSK, MATK, FAK, PYK2, FES, FER, FRK, BRK, SRMS, JAK1, JAK2, JAK3, TYK2, TEC, BMX, BTK, ITK, TXK, SYK or ZAP10.

19. A method of reversibly and allosterically regulating the activity of a non-receptor tyrosine phosphatase comprising:
  inserting into the β10 sheet of the catalytic domain of the non-receptor tyrosine phosphatase a light-responsive construct comprising a first photoreceptive polypeptide domain and a second photoreceptive polypeptide domain, wherein said first and second photoreceptive polypeptide domains:
    (i) are operatively-linked via a flexible linker;
    (ii) independently comprise
      (a) amino acid residues 37-184 of SEQ ID NO:1,
      (b) amino acid residues 40-186 of SEQ ID NO:1,
      (c) a variant of (a) or (b) comprising one or more amino acid substitutions selected from the group consisting of Ile74Val, Ile85Val, Met135Ile, and Met165Ile, or
      (d) a variant of amino acids 37-186 of SEQ ID NO:1 comprising one or more amino acid substitutions selected from the group consisting of Ile74Val, Ile85Val, Met135Ile, and Met165Ile; and
    (iii) are capable of dimerizing with each other thereby producing a fusion protein; and
  exposing the fusion protein to an effective dose of a light to modulate a conformation of the fusion protein, wherein the modulation of the conformation of the fusion protein regulates the activity of the non-receptor tyrosine phosphatase.

20. The method of claim 19, wherein the flexible linker comprises 20 to 100 amino acid residues.

21. The method of claim 19, wherein the flexible linker comprises one or more Gly-Ser-Gly motifs.

22. The method of claim 19, wherein the non-receptor tyrosine phosphatase is PTPN1, PTPN2, PTPN3, PTPN4, PTPN5, PTPN6, PTPN7, PTPN9, PTPN11, PTPN12, PTPN13, PTPN14, PTPN18, PTPN20, PTPN20CP, PTPN21, PTPN22 or PTPN23.

23. The method of claim 19, wherein the non-receptor-tyrosine phosphatase is mammalian.

24. A fusion protein comprising a non-receptor tyrosine phosphatase having inserted in the β10 sheet of the catalytic domain of the non-receptor tyrosine phosphatase a light-responsive construct comprising a first photoreceptive polypeptide domain and a second photoreceptive polypeptide domain, wherein said first and second photoreceptive polypeptide domains:
  (i) are operatively-linked via a flexible linker;
  (ii) independently comprise
    (a) amino acid residues 37-184 of SEQ ID NO:1,
    (b) amino acid residues 40-186 of SEQ ID NO:1,
    (c) a variant of (a) or (b) comprising one or more amino acid substitutions selected from the group consisting of Ile74Val, Ile85Val, Met135Ile, and Met165Ile, or
    (d) a variant of amino acids 37-186 of SEQ ID NO:1 comprising one or more amino acid substitutions selected from the group consisting of Ile74Val, Ile85Val, Met135Ile, and Met165Ile; and
  (iii) are capable of dimerizing with each other.

25. The fusion protein of claim 24, wherein the non-receptor tyrosine phosphatase is PTPN1, PTPN2, PTPN3, PTPN4, PTPN5, PTPN6, PTPN7, PTPN9, PTPN11, PTPN12, PTPN13, PTPN14, PTPN18, PTPN20, PTPN20CP, PTPN21, PTPN22 or PTPN23.

26. The fusion protein of claim 24, wherein the non-receptor tyrosine phosphatase is mammalian.

27. A method of reversibly and allosterically regulating the activity of a Cre recombinase comprising:
  inserting between amino acid residues 59-60 of the Cre recombinase, a light-responsive construct comprising a first photoreceptive polypeptide domain and a second photoreceptive polypeptide domain, wherein said first and second photoreceptive polypeptide domains are the same and:
    (i) are operatively-linked via a flexible linker;
    (ii) comprise
      (a) amino acid residues 37-184 of SEQ ID NO:1,
      (b) amino acid residues 40-186 of SEQ ID NO:1,
      (c) a variant of (a) or (b) comprising one or more amino acid substitutions selected from the group consisting of Ile74Val, Ile85Val, Met135Ile, and Met165Ile, or
      (d) a variant of amino acids 37-186 of SEQ ID NO:1 comprising one or more amino acid substitutions selected from the group consisting of Ile74Val, Ile85Val, Met135Ile, and Met165Ile; and
    (iii) homodimerize with each other thereby producing a fusion protein; and
  exposing the fusion protein to an effective dose of a light to modulate a conformation of the fusion protein, wherein the modulation of the conformation of the fusion protein regulates the activity of the Cre recombinase.

28. The method of claim 27, wherein the flexible linker comprises 20 to 100 amino acid residues.

29. The method of claim 27, wherein the flexible linker comprises one or more Gly-Ser-Gly motifs.

30. A fusion protein comprising a Cre recombinase having inserted in between amino acid residues 59-60 of the Cre recombinase, a light-responsive construct comprising a first photoreceptive polypeptide domain and a second photoreceptive polypeptide domain, wherein said first and second photoreceptive polypeptide domains are the same and:
  (i) are operatively-linked via a flexible linker;
  (ii) comprise
    (a) amino acid residues 37-184 of SEQ ID NO:1,
    (b) amino acid residues 40-186 of SEQ ID NO:1,
    (c) a variant of (a) or (b) comprising one or more amino acid substitutions selected from the group consisting of Ile74Val, Ile85Val, Met135Ile, and Met165Ile, or (d) a variant of amino acids 37-186 of SEQ ID NO:1 comprising one or more amino acid substitutions selected from the group consisting of Ile74Val, Ile85Val, Met135Ile, and Met165Ile; and (iii) homodimerize with each other.

* * * * *